US008420850B2

(12) United States Patent
Duocastella Codina et al.

(10) Patent No.: US 8,420,850 B2
(45) Date of Patent: Apr. 16, 2013

(54) COMPOUNDS FOR THE SYNTHESIS OF BIOSTABLE POLYURETHANE, POLYUREA OR POLYUREA URETHANE POLYMERS

(75) Inventors: Lluis Duocastella Codina, Barcelona (ES); Maria Molina, Barcelona (ES); Ofir Arad, Barcelona (ES); Jose Ignacio Borrell Bilbao, Barcelona (ES); David Sanchez Garcia, Barcelona (ES); Sofia Henriette Petterson Salom, Barcelona (ES)

(73) Assignee: Iberhospitex, S.A, Barcelona (ES)

( * ) Notice: Subject to any disclaimer, the term of this patent is extended or adjusted under 35 U.S.C. 154(b) by 0 days.

(21) Appl. No.: 13/103,187

(22) Filed: May 9, 2011

(65) Prior Publication Data
US 2012/0059117 A1 Mar. 8, 2012

Related U.S. Application Data

(60) Provisional application No. 61/348,124, filed on May 25, 2010.

(30) Foreign Application Priority Data

May 14, 2010 (EP) .................................... 10382122

(51) Int. Cl.
C07C 269/06 (2006.01)
C07C 271/48 (2006.01)
C07C 271/52 (2006.01)

(52) U.S. Cl.
USPC ................................ 560/24; 560/25; 560/27

(58) Field of Classification Search .................. None
See application file for complete search history.

(56) References Cited

U.S. PATENT DOCUMENTS

| 3,272,861 | A | * | 9/1966 | Riggs, Jr. ...................... 564/177 |
| 3,455,940 | A | * | 7/1969 | Stecker ........................ 546/337 |
| 4,179,337 | A |   | 12/1979 | Davis et al. |
| 2003/0220468 | A1 |   | 11/2003 | Lai et al. |
| 2010/0041748 | A1 |   | 2/2010 | Milne et al. |

FOREIGN PATENT DOCUMENTS

| EP | 1 032 605 A1 | 9/2000 |
| EP | 1 710 257 A1 | 10/2006 |
| WO | 98/25938 A1 | 6/1998 |
| WO | 02/098477 A2 | 12/2002 |
| WO | 2005/039489 A2 | 5/2005 |
| WO | 2007/093662 A1 | 8/2007 |
| WO | 2010/040188 A1 | 4/2010 |

OTHER PUBLICATIONS

Extended European Search Report of the priority application EP10382122.9, Oct. 26, 2010.
Espacenet English abstract of WO 2007/093662 A1, Aug. 2007.
Espacenet English abstract of EP 1 032 605 A1, 0-2000.
Bran, Katarina, et al., "Avenanthramides in Oats (*Avena sativa* L.) and Structure-Antioxidant Activity Relationships", *Journal of Agricultural and Food Chemistry*, 2003, 51(3), pp. 594-600.
Gopin, Anna, et al., "Enzymatic Activation of Second-Generation Dendritic Prodrugs: Conjugation of Self-Immolative Dendrimers with Poly(ethylene glycol) via Click Chemistry", *Bioconjugate Chem*, 2006, 17, pp. 1432-1440.
Jensen, Kim B, et al., "Synthesis of Guanidinium-Derived Receptor Libraries and Screening for Selective Peptide Receptors in Water", Chem. Eur. J., 2002, 8, No. 6, pp. 1300-1309.
Haag, Rainer, et al., "Polymer Therapeutics: Concepts and Applications", *Angew. Chem. Int. Ed.*, 2006, 45, pp. 1198-1215.

\* cited by examiner

*Primary Examiner* — Paul A Zucker
(74) *Attorney, Agent, or Firm* — Ladas & Parry LLP

(57) ABSTRACT

The invention comprises compounds which are derived from a drug or a substance with therapeutic properties, and useful as reagents for the synthesis of biostable polymers including said drug in their backbone, namely polyurethanes, polyureas or polyurea urethanes that are biocompatible and biostable. The invention also comprises the processes for preparing the compounds and the polymers, and to the use of these polymers for the manufacture of medical devices.

13 Claims, 2 Drawing Sheets

COMPOUNDS FOR THE SYNTHESIS OF BIOSTABLE POLYURETHANE, POLYUREA OR POLYUREA URETHANE POLYMERS

CROSS-REFERENCE TO RELATED APPLICATION

This application claims the benefit of U.S. Provisional Patent Application Ser. No. 61/348,124 filed May 25, 2010, the contents of which is incorporated herein by reference in its entirety.

The present invention relates to the field of polymers useful for biomedical applications, and to the intermediate materials employed to perform biostable and biocompatible medical devices.

BACKGROUND ART

In the field of implantable devices, such as stents, cardiac valves, cardiac assist devices, reconstructive joint replacement implants, spinal implants, vascular prostheses etc., a critical point is the material employed to manufacture or coat the above mentioned devices. These materials have to be as biocompatible as possible in order to avoid adverse reactions (inflammation, hypersensitivity, foreign-body response, etc.), The devices are made of different kind of materials. Some of them are made of metallic alloys. Others are made of polymeric materials, including polyesters, polyethers, polyamides, silicone polymers, polyethylenes, polyfluoroethylenes, polyurethanes or polyacrylics, among others.

When the devices rest in the body for a long period of time, adverse reactions can be raised, such as acute or chronic inflammation. The adverse reactions are due to the initial damage made by the device, or due to the lack of biocompatibility of the material or of its degradation products. In implantable devices that are designed to be biostable it is possible that in a large period of time a little degradation could start due to deficient mechanical properties of the implant material or for another reason. In this case the degradation products probably would initiate an inflammation and a foreign body response. This biological response against the material leads to the degradation of the material; liberating fragments that may be toxic or may increase the biologic reaction against the material. The degradation would accelerate due to this biological response and could initiate a vicious circle that would generate the failure of the device or another medical issue for the patient. Finally, this process culminates with the failure of the medical device.

In other medical applications, such as in dental or bone regeneration, self-curing formulations based on acrylic polymers are used. These formulations include Eugenol-derived monomers chemically anchored to the polymeric structure and conserve the analgesic and antiseptic properties of the Eugenol. The Eugenol-derived monomers are disclosed in the patent application WO 2007/93662. These monomers are employed as a component of the liquid phase of self-curing formulations for dental implants. However, the use of the acrylic polymers in the field of manufacture of medical devices is limited due to the inherent difficulty to modulate their mechanical properties.

Other medical devices are conceived to be absorbed by the tissues to finally release an active ingredient. For this purpose some patches or implantable devices are made of polymers including drugs as monomers. One example of this is set in the patent document EP 1032605 B1, wherein in a polyanhydride-based polymer a drug-derived monomer is linked to the polymer skeleton through labile bonds. The object of the polyanhydrides disclosed in EP 1032605 B1 is that the drug-derived monomer is released to deliver the drug. This type of polymers are useful for medical devices which have to rest in the body for short periods of time, since the device is finally disintegrated and, for example, they are not suitable for the construction of cardiac valves. The polyanhydride has a disadvantage similar to the polyacrylic polymers, the range of their mechanical properties is narrow and difficult to modulate.

Examples of polymeric constructions with the aim of finally releasing a therapeutic or diagnostic agent to a preferred organ or target are widely disclosed in the document by Haag et al., "Polymer Therapeutics: Concepts and Applications", *Anqewandte Chemie,* 2006, vol. 45, pp. 1198-1215. This document is a review showing polymer-protein conjugates, drug-polymer conjugates, as well as supramolecular drug-delivery systems. The drug or the protein of the conjugates is linked with the polymeric structure as an appended compound.

A further example is WO 2010/040188 which discloses a biodegradable polymer comprising releasable bioactive moieties being pendant from and covalently bonded to the polymer backbone, wherein the biodegradable polymer backbone is formed from monomeric units that are each coupled via a biodegradable moiety, and wherein the bioactive moieties are capable of being released at rate equal or faster than the rate of biodegradation of the polymer backbone. The polymers of the present invention on the contrary are biostable and present the drugs either as part of the polymer backbone or as terminal monomer units. The polymers disclosed in WO 2010/040188 can be used in the preparation of an implantable scaffold, stent or biomedical coating or dressing or adhesive. In addition WO 2010/040188 discloses monomer-bioactive moiety conjugates suitable in preparing biodegradable polymers comprising a drug and presenting two terminal functional groups capable of undergoing polymerization, as well as some intermediate compounds useful for the synthesis of monomer-bioactive moiety conjugates which are different from the monomer compounds of the present invention.

Also WO 02/098477 discloses bioactive fluoroalkyl surface modifiers (polymers) containing biologically active molecules, such as pharmaceuticals, for use in admixture with a base polymer for coating or forming medical devices. The bioactive fluoroalkyl surface modifiers disclosed in WO 02/098477 differ from the polymers of the present invention in that the biologically active molecules grafted to the so called linkB segment within the bioactive fluoroalkyl surface modifier are pendent, and directly and covalently linked without any spacer.

US2010/0041748 discloses fatty acid acetylated salicylate derivatives, fatty acid acetylated diflunisal derivatives and fatty acid acetylated triflusal derivatives, a process for their synthesis and its use for the treatment or prevention of inflammatory disorders. US2010/0041748 discloses as well intermediates compounds involved in the synthesis of the mentioned derivatives which present a similar but different structure from the monomer compounds of the present invention, differing at least in the type of bond linking the drug to the spacer.

EP 1710257 discloses hyaluronic acid derivatives in which an anti-inflammatory drug is bound to hyaluronic acid through a covalent bond via a spacer having a biodegradable region, and a production process thereof, in which a spacer is introduced into a drug in advance and thereafter the resulting product into hyaluronic acid. The intermediate compounds involved in said process and disclosed in EP 1710257 are however different from the monomer compounds of the present invention, and differ at least in the type of bond linking the drug to the spacer.

U.S. Pat. No. 4,179,337 discloses peptides and polypeptides coupled to polymers which posses a substantially linear ethereal or carbon carbon backbone, for instance polyethylenglycol and polypropylenglycol, which are substantially non-immunogenic and retain a substantial proportion of the desired physiological activity of the peptide or polypeptide. Some of the disclosed compounds have a similar but different structure from the monomer compounds of the present invention, and differ either in the type of bond linking the drug to the spacer and/or in the type of drug being different from a peptide or polypeptide.

US 2003/0220468 discloses derivatives of nonsteroidal anti-inflammatory agent which provide the therapeutic effect of the drug while causing a much lower incidence of the common side-effects. Some of the derivatives present a similar structure to the monomer compounds of the present invention, but are however different, differing at least in the type of bond linking the drug to the spacer.

U.S. Pat. No. 5,589,563 relates to surface-active endgroups (SMEs) containing polymers in which the endgroups contain covalently bonded surface active groups such that the surface activity of said polymers is controlled by said surface active groups. The SMEs groups improve the biostability of the polymers, such as polyurethanes or polyurethaneureas, which can be formed into articles to be implanted in humans or animals. Preferred SMEs are monofunctional polyethylenoxide-amines, monofunctional polyethylenoxide-alcohols, polydimethylsiloxane-amines and dodecylamines.

In the PCT application WO 2005/39489 some polymers useful to locally administer anti-inflammatory substances are disclosed. These polymers comprise anti-inflammatory substances embedded into the backbone of the same. The substances are finally released into the body to attain their effect. The document presents a wide range of putative linkages between the anti-inflammatory substances and the backbone of the polymer, and it indicates also that the release of the anti-inflammatory substances is done in a period of at least about 2 hours to about years, stating that the degradation properties may be controlled by modifying the specific linkage between the anti-inflammatory substances and the backbone of the polymer. Nonetheless, the document only shows combinations of breakable linkages leading to hydrolysis of the compounds from 8 hours to 2 months.

Thus, compounds that allow minimizing the adverse reactions of medical devices in the body are needed. In particular, there is a need of compounds that can be used for the manufacture of medical devices with the aim of resting for a long time in the body while avoiding the adverse reactions occasioned by the implant to the organism. Another property that is very important for these materials is that their mechanical properties have to fit exactly to the wanted application; otherwise the material will degrade with time.

SUMMARY OF THE INVENTION

The compounds and polymers of the present invention represent a solution to the above-mentioned problems since they are stable in the biological or body environment for a long period of time. At the same time they do not have any cytotoxicity or adverse effects for the health. Additionally, their mechanical properties can be widely and easily modulated to adjust to the specific biomedical application. The drug or drugs integrated in-between the proposed compounds and polymers are not released. Safe and efficient long-time resting medical devices can be obtained with this kind of compounds.

Thus, in a first aspect the invention relates to a compound of formula (I) or a salt thereof, $$(X—S)_m\text{-}D \qquad\qquad (I),$$

wherein:
—D is a radical derived from a drug susceptible to form at least an amide bond, an urea bond, a carbamate bond, an ether bond, a thioamide bond, a disulfide bond, a siloxane bond, a carbonate bond, an amine bond, and an ester bond with S;
—S— is a biradical consisting of a branched or unbranched, saturated or unsaturated $C_2$-$C_{299}$ hydrocarbon chain, bonded for one extrem to radical X and for the other extrem susceptible to form at least an amide bond, an urea bond, a carbamate bond, an ether bond, a thioamide bond, a disulfide bond, a siloxane bond, a carbonate bond, an amine bond, or an ester bond with D, said hydrocarbon chain having at the extreme forming the bond with D an atom or group of atoms selected from the group consisting of an oxygen atom, a sulphur atom, a radical of formula —$NR_2$— or a radical of formula —CO—, said hydrocarbon chain optionally having one or more non-terminal carbon atoms replaced by an oxygen atom, a sulphur atom, or group of formula —$NR_2$—, and wherein optionally at least one hydrogen atom of said hydrocarbon chain is substituted by at least one radical selected from the group consisting of an halogen or a $C_1$-$C_8$-alkyl radical;
—$R_2$ is a radical selected from the group consisting of hydrogen, and a linear or branched $C_1$-$C_8$-alkyl;
—X is a radical selected from the group consisting of —$NH_2$, —NCO, and —OH; and m is an integer from 1 to 4.

According to a particular embodiment of compound of formula (I), when m is 1, —S— is bonded for one extreme to radical X and for the other extreme it forms a bond selected from an urea bond, a carbamate bond, an ether bond, a thioamide bond, a disulfide bond, a siloxane bond, a carbonate bond and an amine bond with D, and D is different from a peptide or polypeptide.

According to another particular embodiment of compound of formula (I), when m is 1, —S— is bonded for one extreme to radical X and for the other extreme it forms a bond selected from an urea bond, a carbamate bond, an ether bond, a thioamide bond, a disulfide bond, a siloxane bond, a carbonate bond and an amine bond with D, with the proviso that when said bond is a carbamate bond, D is different from a peptide or polypeptide.

The compounds of formula (I) may be polymerized to form polyurethanes, polyureas or polyurea urethanes which are stable in the organism. The inventors surprisingly found that the combination of the bond between D and S, as well as the implicit aromaticity and hydrophobicity of the D radical, lead to polymeric compounds which are not hydrolyzed in the body environment. Moreover, they are prepared, by means of the selection of the radical X, to perform reactions with polyurethane pre polymers, wherein a prepolymer is to be understood as a polymer obtained from the reaction of isocyanate compounds and polyol compounds, this polymer can be then further reacted to obtain polyurethane or polyurea urethane polymers having a molecular weight greater than that of the prepolymer. Thus, the compounds of formula (I) lead to a polyurethane or a polyurea urethane polymer, or to a polyurea polymer, from which multiple medical devices and uses can be derived, and which remain intact for a long time when introduced into the body.

The water absorption and the consequent hydrolysis are reduced due to the aromaticity and hydrophobicity obtained by the presence of D. D gives rigidity and good mechanical properties to the final polymer that helps to avoid the degradation of implants.

In polymers that are designed to be biostable it is possible that in a large period of time a little degradation could start due to deficient mechanical properties or another reason. In this case the degradation products probably would initiate an inflammation and a foreign body response. The degradation would accelerate due to this biological response and could initiate a vicious circle that would generate the failure of the device or another medical issue for the patient. In the context of the present invention biostable means that the polymer is not degraded during its operative live in the body, or weakly degrades. In a more concrete definition, the biostable polymers are not mechanically or chemically modified when submitted to accelerated oxidative conditions for long periods of time (1-2 months or more), being those determined by UNE EN ISO 10993-13 (Biologic evaluation of sanitary products Identification and quantitative determination of the degradation products of the biomedical sanitary products).

If the biostable polymer is made with an anti-inflammatory drug, the inventors surprisingly found that the polymer infers an anti-inflammatory effect, although the drug is not released and is stably retained in the backbone of the polymer. Anyway, if the biostable polymer is made with an anti-inflammatory drug, the drug released in case of initiation of the degradation process could help to reduce or even stop the degradation due to the biological response described above. All these features make the polymers of the invention of great interest in the field of medicine.

Biostable polymers made with drugs with different therapeutical activities would have the advantage of being made with a very well studied raw material (a drug or an active metabolite of a drug); and in case of degradation of the polymer the liberated drug will treat the medical problem of the patient at that point.

A second aspect of the invention is a process for preparing the compound of formula (I) as defined above, which comprises the steps of:
a) reacting a drug susceptible to form at least an amide bond, an urea bond, a carbamate bond, an ether bond, a thioamide bond, a disulfide bond, a siloxane bond, a carbonate bond, an amine bond, or an ester bond with a compound of formula (III)

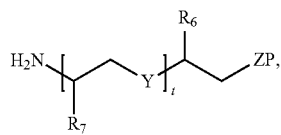
(III)

wherein:
—Y is an atom or a group of atoms independently selected from the group consisting of $CH_2$, NH, O, S;
-t is an integer ranging from 0 to 99;
—Z is an atom or group of atoms selected from the group consisting of NH and O; and
—P is a radical which is a protective group selected from the group consisting of t-butyloxycarbonyl (BOC), benzyl, allyl, t-butyl(chloro)diphenylsilane and $SiR_3R_4R_5$, wherein $R_3$, $R_4$, and $R_5$ are radicals equal or different and selected from the group consisting of phenyl or linear or branched $C_1$-$C_4$-alkyl;

—$R_6$ and $R_7$ are radicals equal or different and selected from the group consisting of hydrogen and methyl;
with the proviso that if Z is equal to 0, P is selected from the group consisting of t-butyl(chloro)diphenylsilane and $SiR_3R_4R_5$, and if Z is equal to N, P is a radical selected from the group consisting of t-butyloxycarbonyl (BOC), benzyl and allyl, and
b) removing the radical protecting group by reaction of the compound obtained in step a) with an hydrogen halide in an appropriate solvent; to give a compound of formula (I);
or, alternatively,
c) reacting a drug susceptible to form at least an amide bond, an urea bond, a carbamate bond, an ether bond, a thioamide bond, a disulfide bond, a siloxane bond, a carbonate bond, an amine bond, or an ester bond, with a compound formula (IV), wherein T is an halogen atom;

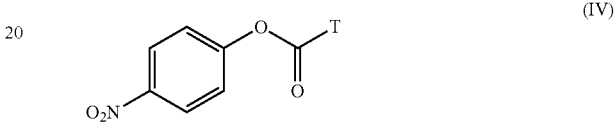
(IV)

d) reacting the compound obtained in step c) with a compound of formula (III); and
e) removing the radical protecting group P by reaction of the compound obtained in step d) with an hydrogen halide; to give a compound of formula (I)
or, alternatively,
f) reacting a drug susceptible to form at least an amide bond, an urea bond, a carbamate bond, an ether bond, a thioamide bond, a disulfide bond, a siloxane bond, a carbonate bond, an amine bond, and an ester bond, with a compound of formula $(COW)_2$, wherein W is an halogen, in the presence of a compound of formula $C_1$-$C_4$ alkyl-O-Q, wherein Q is an halogen;
g) reacting the compound obtained in step f) with sodium azide; and
h) hydrogenating the compound obtained in step d); to give a compound of formula (I);
and, if needed, repeating steps a) and b); or c), d) and e); or f), g) and h); or a combination of a) and b) with c) d) and e); or a combination of a) and b) with f), g) and h); or a combination of c) d) and e) with f), g) and h); to give a compound of formula (I) with m=2, 3 or 4;
wherein, optionally, the X radical of the compound of formula (I) obtained is transformed into another X radical of the compound of formula (I); and, optionally, the X1 or X2 radical of the compound of formula (Ia) obtained is transformed into another X1 or X2 radical of the compound of formula (Ia).

The compound of formula (I) with m=2 is the compound of formula (Ia);

X1-S1-D-S2-X2     (Ia).

A third aspect of the invention is a process for preparing polyurethane, a polyurea or a polyurea urethane polymer comprising the steps of:
a) reacting an excess of a diisocyanate or a polyisocyanate (compound comprising at least two isocyanate groups (—NCO)) with a compound comprising at least two —OH groups to obtain a polyurethane compound, which is also named prepolymer of polyurethane; and
b) mixing the compound obtained in step a) with at least one compound of formula (I) as defined above.

For the obtention of the prepolymer of polyurethane of step a) any compound of formula (I) (Ia), etc. according to the invention may also be used. In such a way, a compound of formula (Ia) wherein X1 and X2 are —OH radicals, thus acting as polyol compound, may be reacted with an excess of another compound of formula (Ia) in which X1 and X2 are —NCO radicals to obtain a polyurethane prepolymer, which then can be reacted with another compound of formula (I) to obtain a polyurethane with a greater molecular weight, or a polyurea, or a polyurea urethane polymer.

In a fourth aspect, the invention relates to a polyurethane, polyurea or a polyurea urethane compound obtainable by the process as defined above.

A polyurea is obtained when both a polyol component and a chain extender having —NH$_2$ functionality are reacted.

A polyurea urethane is obtained when a polyol component or a chain extender are reacted, one being an amine with at least two —NH$_2$ functionality the other having at least two —OH functionalities.

The polyurethanes, polyureas or polyurea urethanes obtained having the compounds of formula (I) as forming part of its backbone, represent a very interesting material to further manufacturing a wide spectrum of medical devices and other products for medical appliance. They have a wide applicability derived from the fact that their properties can be easily and extensively modified by varying the ratio between the soft and the hard segment, namely the ratio of the polyol compound versus the chain extender and the isocyanate compound reacted with the compounds of formula (I) of the invention.

Thus, another aspect of the invention relates to medical devices made of the polyurethane, polyurea or polyurea urethane compounds of the invention.

Another aspect of the invention relates to coatings for medical devices comprising the polyurethane, polyurea or polyurea urethane compound of the invention. The main application of the biostable polyurethane, polyurea or polyurea urethanes of the invention is as drug eluting stent (DES) coating. The DES implants need a coating to elute a drug with anti-inflammatory, antiproliferative, or pro-endothelizing activity, among other possible therapeutic activities. The polymer is needed as a vehicle for the elution and control of the kinetic of liberation of the drug into the blood stream. However inflammatory and hypersensitivity reactions are attributed to actual polymers. These undesired reactions are added to the inflammation due to the medical device introduction. The biostable polyurethanes, polyureas and polyurea urethanes of the present invention are designed not to degrade and their mechanical properties can be modulated to adequate exactly to the desired application. Additionally these polymers can be charged with a drug for a controlled release into the blood stream. The polymers of the present invention are made with a drug in their backbone that is not released in normal conditions but in case that the degradation of the material begins, the released d rug would be therapeutic.

DETAILED DESCRIPTION OF PARTICULAR EMBODIMENTS

Figure 1:
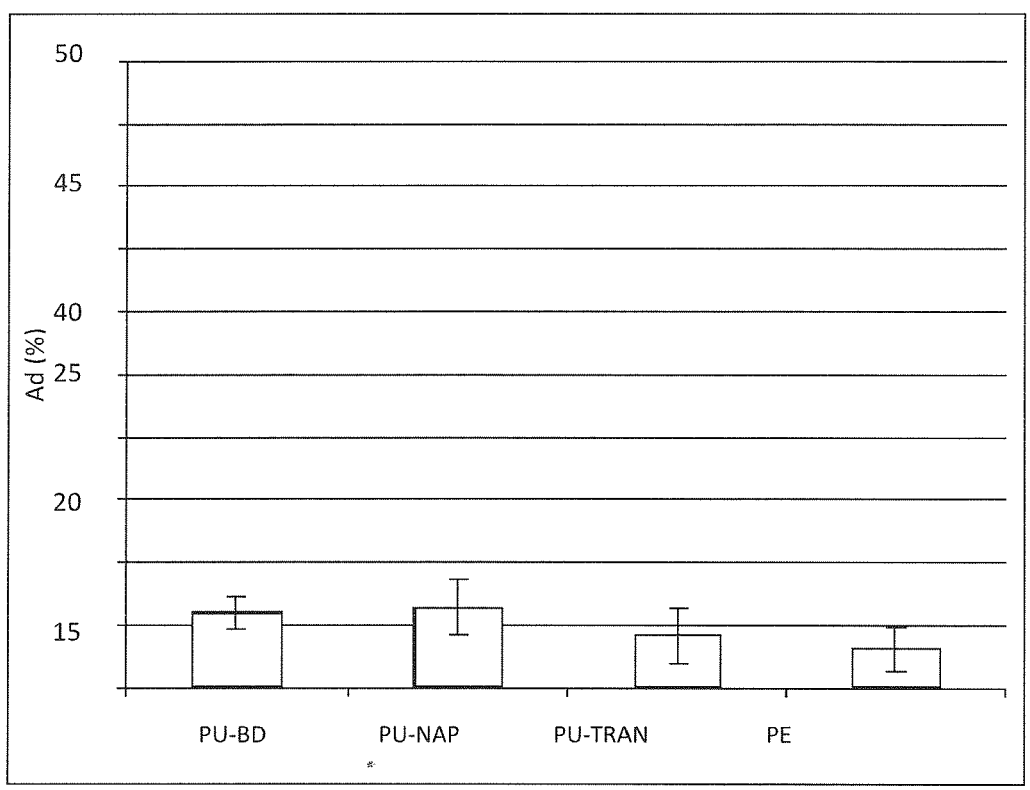
FIG. 1, related with Example 7, is a bar diagram showing the platelet adhesion (%) observed on the surfaces of polyurethane polymers of the invention. Ad(%) means percentage of adhesion; PE is polyethylene; PU-BD is a polyurethane according to example 5.2 with 1,4-butanediol as the chain extender; PU-NAP is a polyurethane according to example 5.2 with a compound of formula (Ie) derived from naproxen as chain extender; and PU-TRAN is polyurethane according to example 5.2 with a compound of formula (Id) derived from tranilast as chain extender.

Some definitions are included with the aim of facilitating the understanding of the invention.

In the sense of the invention a "drug" is any chemical substance used or able to be used in the treatment, cure, prevention, or diagnosis of disease or used to otherwise enhance physical or mental well-being. A medication or medicine is a drug taken to cure and/or ameliorate any symptoms of an illness or medical condition, or may be used as preventive medicine that has future benefits but does not treat any existing or pre-existing diseases or symptoms. The term "drug" includes also any active metabolite of a drug, which is formed into the body due to the metabolism of said drug, and that maintains or provides a biological activity. All these "drugs" have functional groups adapted, or that can be chemically modified to perform linkages with a polymeric backbone.

A "polyurethane" is any polymer consisting of a chain of organic units joined by urethane (carbamate) bonds (links). Polyurethane polymers are formed through step-growth polymerization by reacting a monomer containing at least two isocyanate (—NCO) functional groups with another monomer containing at least two hydroxyl (alcohol; —OH) groups (polyol compound). The isocyanate can be aromatic or aliphatic in nature. It can be monomer, polymer, or any variant reaction of isocyanates or a prepolymer. The prepolymer can be made of an hydroxyl-terminated polymer resin.

A "polyol" is a compound having at least two hydroxyl (—OH) groups or at least two amine (—NH$_2$) groups. In general they are compounds with a molecular weight comprised between 500 and 5000 daltons (Da). Although the term polyol refers in general to compounds with two or more alcohol groups or radicals which can be reacted for example with an isocyanate compound, in the field of polyurethanes it is widely accepted that the compounds with two or more amine groups can also be designated as the "polyol component" of a polyurethane, polyurea or polyurea urethane polymer. The polyol in a polyurethane, polyurea or polyurea urethane polymer is also referred as the "soft segment" of the polymer. On the other hand the isocyanate compound and the chain extender used to react with the soft segment are named "hard segment".

In the context of the present invention the compounds of formula (I) may be used as the "soft segment" if reacted with an isocyanate compound to form a prepolymer. The compounds of formula (I) may also be used as chain extenders to be reacted with a prepolymer in the synthesis of polyurethane.

A "chain extender" in a reaction to obtain a polyurethane is any low molecular weight hydroxyl and amine terminated compound, able to react with any prepolymer or polymeric fragment previously formed, and propitiating the extension of the said polymer.

A "polyurea polymer" is a polymeric compound comprising a chain of organic units joined by urea chemical bonds. They can be derived from the reaction product of an isocyanate component and a synthetic resin blend component through step-growth polymerization. The isocyanate can be aromatic or aliphatic in nature. It can be monomer, polymer, or any variant reaction of isocyanates or a prepolymer.

A "polyurea urethane polymer" is a polymer comprising a chain of organic units joined by urethane (carbamate) chemical bonds (links) and urea (carbamide) chemical bonds.

As "prepolymer" is to be understood as any polymer obtained from the reaction of isocyanate compounds and polyol compounds, which further will continue to react with a "chain extender" to obtain greater polymeric compounds.

The compounds of formula (I) of the invention represent a good option for the achievement of polymers being resistant to the hostile environment of the body. As above exposed, the combination of the D radical and the —S— biradical, leads to polyurethanes, polyureas and polyurea urethanes, which are difficult to be hydrolyzed. With the aim of further reinforcing the stability of the molecules, preferred compounds of formula (I), $(X-S)_m$-D, are those in which between D and —S— an amide bond or a carbamate bond is done.

The drug or an active metabolite of a drug is preferably a substance with anti-inflammatory and/or anti-proliferative properties. In some cases, inherently to the nature of the substance, analgesic effects may be observed. Other therapeutic effects may be derived from the drugs comprised in the compounds of formula (I) of the invention.

In the sense of the invention, a chemical "bond" is an interaction between atoms or molecules and allows the formation of chemical compounds, which contain two or more atoms.

When the substance forms at least an ester bond, it is important to note that this ester should not be an easily hydrolysable ester and it should not be combined with other hydrophilic components that could accelerate its degradation. As above exposed, the juxtaposed effect of the hydrophobicity and/or aromacity of the drug and the nature of the biradical —S—, will lead to the establishment of an ester bond with biostability properties, that is, to a chemical compound difficult to be hydrolyzed in the body environment.

In another preferred embodiment, the compounds of formula (I) comprise as the $C_2$-$C_{299}$ hydrocarbon chain of the S part; a $C_2$-$C_{199}$ hydrocarbon chain. In a more preferred embodiment the hydrocarbon chain is a $C_2$-$C_{50}$ hydrocarbon chain. In addition, another more preferred embodiment is a $C_2$-$C_{19}$ hydrocarbon chain, preferably a $C_2$-$C_8$ hydrocarbon chain. In a more preferred embodiment, the hydrocarbon chain is a $C_2$ hydrocarbon chain, preferably the chain being the following: —CH$_2$—CH$_2$—.

Alternatively, the $C_2$-$C_{299}$ hydrocarbon chain is a $C_2$-$C_{299}$ hydrocarbon chain with non-terminal carbon atoms replaced by oxygen atoms, and which has formula (II), wherein n is an integer ranging from 1 to 99, and the bonds crossed with sinusoidal lines represent the linkage point with the atoms or group of atoms (e.g. NH$_2$) that are finally forming any bond with the drug D or the radical X.

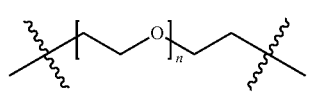

(II)

Other examples of the $C_2$-$C_{299}$ hydrocarbon chain include other chains having at one end an oxygen atom. Said hydrocarbon chain may be substituted by at least one radical selected from the group consisting of halogen and $C_1$-$C_8$-alkyl, such as methyl, ethyl or propyl. Examples of the above mentioned $C_2$-$C_{299}$ hydrocarbon chains are polyethylene glycol, polypropylene glycol or polytetramethylene glycol.

In another preferred embodiment the compounds of formula (I) comprise as radical X an amino (—NH$_2$) radical.

Preferred compounds of formula (I) are those having formula (Ia),

X1-S1-D-S2-X2 (Ia), in which D is a biradical derived from a drug or a substance with therapeutic properties, such as an active metabolite of a drug.

The above mentioned biradical D in formula (Ia) forms two bonds with two biradicals (S1, and S2), said bonds being selected from the group consisting of an amide bond, an urea bond, a carbamate an ether bond, a thioamide bond, a disulfide bond, a siloxane bond, a carbonate bond, an amine bond, and an ester bond. Preferred bonds are an amide bond and a carbamate bond. In the compounds of formula (Ia), —X1 and —X2 are equal or different radicals having the same meaning as —X; —S1 and —S2 are equal or different radicals having the same meaning as —S; and -D, —X, and —S have the same meaning as defined above for compounds of formula (I).

The compounds of formula (Ia), comprising the two radicals X1 and X2, are of special interest since they can be used as chain extenders in the polymerization reaction leading to a polyurethane, a polyurea or a polyurea urethane polymer. These compounds of formula (Ia) derive from compounds of formula (I) with m being equal to 2. If additionally, D forms a third or a fourth bond, the resultant polymers will have a part of cross-linking structures. More specifically, when in a compound of formula (I) m takes values of 3 or 4, the resulting compound may act as a cross-linker agent to obtain a polymeric structure with branched fragments. Higher level of cross-linking is related in higher hardness and biostability. These properties are positive for many applications as implants.

In a preferred embodiment D is a radical derived from a drug which includes in its chemical structure an aromatic group, namely an aryl group, and at least a carboxylic group or an ester of said carboxylic group, Ar—COO—($C_1$-$C_3$)-alkyl; and at least a reactive alcohol radical (—OH) or a radical with formula —O—($C_1$-$C_3$)-alkyl. Ar is the aromatic group of the drug. Examples of ($C_1$-$C_3$)-alkyl include methyl, ethyl, propyl and isopropyl radicals. As "aryl" is to be understood any C-radical derived from one of the known 1-4 aromatic ring systems, the rings being isolated or partially/totally fused and having 5-6 members; being each member independently selected from C, CH, N, NH, O, and S. Examples of aryl groups included, but are not limited to monocyclic, bicyclic or tricyclic aromatic ring system, for example phenyl, 1-naphtyl, 2-naphtyl, thiophenyl, indolyl and dioxole rings fused to the benzyl, naphtyl, thiophenyl and indolyl ring, which may be substituted with one or more alkyl, alkoxyl, halo, or amino groups, as well as with one or more ethers, esters or amides of said groups.

In a more preferred embodiment D is a radical derived from a drug, an active metabolite of a drug, or a substance with anti-inflammatory, anti-proliferative and/or other therapeutic properties and selected from the group consisting of homovanillic acid, 4-hydroxicinnamic acid, indometacin, fendosal, diflunisal, p-coumaric acid, acemetacine, bentiromide, phenolphtalein, repaglinide, sarpogrelate, tiropropic acid, tiratricol, vanillic acid, 3-fluoro-4-hydroxyphenylacetic acid, iophenoic acid, allenolic acid, anacardic acid, cinnametic acid, cinmetacine, clometacine, ferulic acid, mycophenolic acid, salicylic acid, methyl salicylate, rhein, naproxen, and tranilast.

In a more preferred embodiment D is a radical derived from a substance selected from the group consisting of methyl salicylate, naproxen and tranilast.

All these substances include in their structure, chemical groups or at least one radical, which can form with the biradical —S1- or —S2- (if more than one is present) the chemical bonds previously disclosed.

In a preferred embodiment, the compound of formula (I) is the compound of formula (Ib)

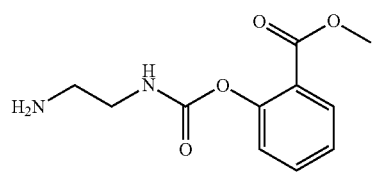

(Ib)

In another preferred embodiment the compound of formula (I) is the compound of formula (Ic)

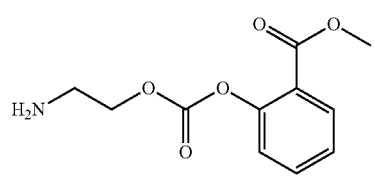

(Ic)

Compounds of formula (Ib) and (Ic), derived from a compound of formula (I) wherein m is equal to 1 are of special interest since they act as blocking agents in a polymeric reaction. Acting as blocking agents, these compounds serve to control the molecular weight of the resultant polymer, and are introduced in the pool reaction when lower molecular weights are desired.

Preferred embodiments including a radical D which forms two bonds with the biradicals —S1- and —S2-, i.e. preferred embodiments of compounds of formula (Ia), are the compounds of formula (Id) and (Ie):

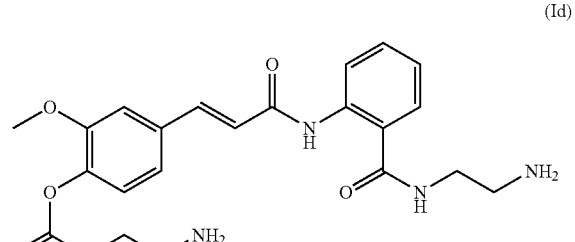

(Id)

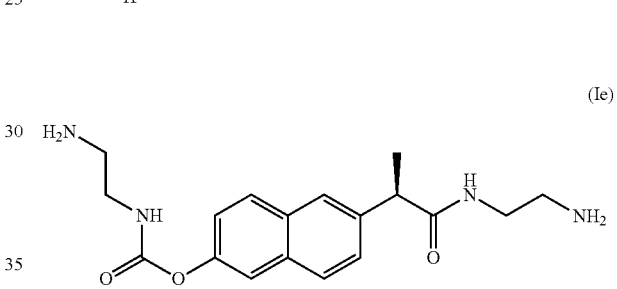

(Ie)

In another preferred embodiment, the compounds of formula (Ia), are those which include as —S1- and —S2- a biradical consisting of a branched or unbranched, saturated or unsaturated $C_2$-$C_{299}$ hydrocarbon chain, having one or more non-terminal carbon atoms replaced by an oxygen atom. In a preferred embodiment, these compounds have the formula (If)

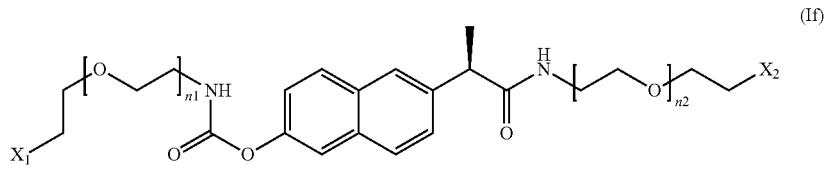

(If)

wherein:
  $n_1$ and $n_2$ are equal or different integers ranging from 1 to 99; and
  X1 and X2 are equal or different radicals and selected from the group consisting of —$NH_2$, —NCO, and —OH.

As illustrated below by means of the examples, the compounds of formula (I) may be synthesised by means of the process comprising the steps of:

a) reacting a drug or substance with therapeutic properties and susceptible to form at least an amide bond, an urea bond, a carbamate, an ether bond, a thioamide bond, a disulfide bond, a siloxane bond, a carbonate bond, an amine bond, and an ester bond, with a compound of formula (III), and

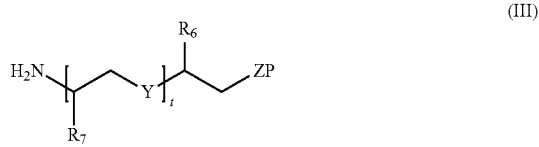

(III)

b) removing the protecting group by reaction of the compound obtained in step a) with an hydrogen halide in an appropriate solvent;
or, alternatively,
c) reacting a drug or a substance with therapeutical properties and susceptible to form at least an amide bond, an urea bond, a carbamate bond, an ether bond, a thioamide bond, a disulfide bond, a siloxane bond, a carbonate bond, an amine bond, or an ester bond, with a compound formula (IV);

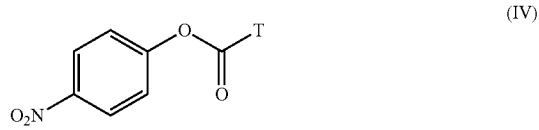

(IV)

d) reacting the compound obtained in step c) with a compound of formula (III); and then
e) removing the radical protecting group P by reaction of the compound obtained in step d) with an hydrogen halide;
or, alternatively,
f) reacting a drug or substance with therapeutic properties and susceptible to form at least an amide bond, an urea bond, a carbamate bond, an ether bond, a thioamide bond, a disulfide bond, a siloxane bond, a carbonate bond, an amine bond, or an ester bond, with a compound of formula $(COW)_2$, wherein W is an halogen, in the presence of a compound of formula $C_1$-$C_4$ alkyl-O-Q, wherein Q is an halogen;
g) reacting the compound obtained in step f) with sodium azide; and then
h) hydrogenating the compound obtained in step g).

If needed, the steps a) and b); or c), d) and e); or f), g) and h) may be repeated in order to obtain a compound of formula (I) having more than one terminal reactive group, or, which is the same, more than one radical X selected from the group consisting of —$NH_2$, —NCO, and —OH. Alternatively, the process may be performed by combining the steps a) and b) with c) d) and e); or by combining the steps a) and b) with f), g) and h); or making a combination of steps c) d) and e) with f), g) and h).

When the compound of formula (III) is used and the radical protective groups have to be removed, a hydrogen halide selected from the group consisting of HCl and HBr is used. Nonetheless, the removing may be performed directly by bubbling the hydrogen halide gas, using the hydrogen halide in an organic solvent, using acidic solutions of inorganic acids, such as HCl or HBr, or using organic acids with a strong acidity.

The step of removing the protective groups is preferably performed in an organic solvent which can be an alcohol (methanol), or a mixture of dichloromethane and methanol.

When a hydrogenation reaction is carried out, an adequate catalyst such as Pd/C may be used.

Preferably, the process for preparing compounds of formula (I) is performed with a drug or a substance with antiinflammatory, anti-proliferative and/or other therapeutic properties, which is reacted in order to form two bonds, said bonds selected from an amide bond, an urea bond, a carbamate bond, an ether bond, a thioamide bond, a disulfide bond, a siloxane bond, a carbonate bond, an amine bond, and an ester bond.

The process for preparing compounds of formula (I) of the invention may further include steps in which at least one X radical of the compound of formula (I) obtained, is transformed into another X radical of the compound of formula (I). By means of these additional steps the radical X being an amino (—$NH_2$) radical is transformed to a radical X being an isocyanate radical (—NCO).

Particularly, for the transformation of the —$NH_2$ radical to a —NCO radical the compound of formula (I) is reacted with hexamethyldisilazane (HMDS), and then with triphosgene, although other known methods, such as the Hofmann rearrangement may be applied.

Preferred halogen atoms of formulas $(COW)_2$ and $C_1$-$C_4$ alkyl-O-Q are selected from Cl and Br.

The compounds of formula (I) of the invention are used in a process for preparing polyurethane, polyurea or polyurea urethane polymers, in which an excess of a compound comprising at least two isocyanate groups is reacted with a compound comprising at least two —OH groups or —$NH_2$ (also named polyol compound) to obtain a prepolymer of polyurethane, a polyurea or a polyurea urethane, and then reacting said prepolymer with at least one compound of formula (I) as defined above.

Preferably, the process for preparing polyurethane polymers is carried out with a diisocyanate or a polyisocyanate compound, which is selected from the group consisting of isophorone diisocyanate (IPDI), hexamethylene diisocyanate (HDI), methylene diphenyl diisocyanate (MDI) and toluendiisocyanate (TDI) or a compound of formula (I) with at least two NCO functionalities as indicated above.

Preferred compounds comprising at least two —OH groups or —$NH_2$ groups are selected from the group consisting of polyethers, polycarbonates, polydimethylsiloxanediol, polybutadienediol, polyesters and polyamides, or a mixture thereof. Also as above indicated, polyols made with a compound of formula (I), with at least two —OH or —$NH_2$ groups could be used.

Preferably the polyethers used are selected from the group consisting of polypropilenglycol, poly(1,4-tetramethylene) glycol, poly(1,5-pentanediol), and polyhexamethylene oxide, or a mixture thereof.

Preferably the polycarbonates used are selected from the group consisting of poly(1,6-hexacarbonate)diol and poly(1, 5-pentacarbonate)diol, or a mixture thereof.

The process for preparing polyurethane, polyurea or polyurea urethane polymers may be optionally carried out in the presence of an organic solvent selected from the group consisting of ethyl acetate, butyl acetate, toluene, dimethylformamide (DMF), dimethylacetamide (DMAc) and methyl ethyl ketone (MEK).

As mentioned above, medical devices made of the polyurethane compounds, polyurea or polyurea urethane compounds form also part of the invention. Preferably, the medical device is a cardiac valve.

Other application of the polymers of the invention is as coating for a medical device, preferably for a vascular stent.

Other suitable applications of the polymer compounds of the invention include the manufacture of other medical devices, such as implants selected from valves, pacemakers, breast implants, gastric balloons, glucose sensors, drug delivery pads, embolic agents, orthopedic devices, and scaffolds for in-vivo or in-vitro tissue regeneration or dialysis filters, among others.

The compounds of formula (I) of the invention in which the radical X (X1 and/or X2) is an amino group may be reacted with any dicarboxylic acid to form polyamides. These polyamides may, in turn, be reacted with any compound comprising at least two isocyanate radicals in order to get the "prepolymer" for the synthesis of a greater polyurethane compound.

Thus, with the compounds of formula (I) high molecular weight polymeric compounds, such as polyurethanes, may be obtained.

Throughout the description and claims the word "comprise" and variations of the word, are not intended to exclude other technical features, additives, components, or steps. Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim, and shall not be construed as limiting the scope of the claim. Furthermore, the present invention covers all possible combinations of particular and preferred embodiments described herein.

EXAMPLES

| Abbreviations: | |
|---|---|
| BD | 1,4-butanediol |
| BOC | tert-butoxycarbonyl |
| DCM | dichlormethane |
| DIPEA | N,N-diisopropylethylamine |
| DMAP | 4-dimethylaminopyridine |
| DMF | N,N-dimethylformamide |
| Hex | Hexane |
| GPC | Gel Permeation Chromatography |
| MEK | methyl ethyl ketone |
| PDMS | polydimethylsiloxane |
| PyBOP | benzotriazol-1-yl-oxytripyrrolidinophosphonium hexafluorophosphate |
| THF | tetrahydrofuran |
| TLC | Thin Layer Chromatography |

The yields of the reactions are expressed as the percentage by weight of the product obtained in respect of the total weight of the compounds intervening in the said reaction.

Example 1

Preparation of a Compound of Formula (I) Derived from Methyl Salicylate with Amine Functionality (Compound 1b)

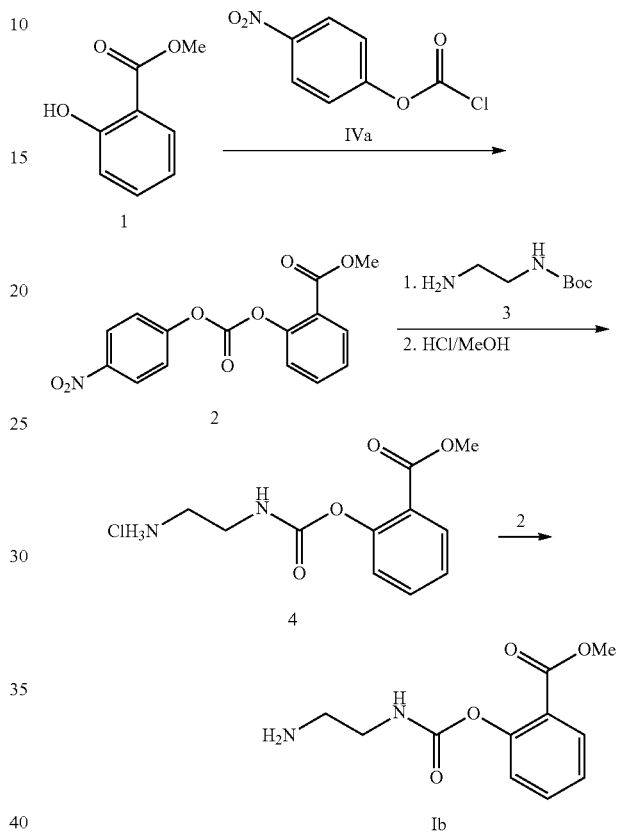

Me: methyl
MeOH: methanol

Compound 1 (1.5 g, 10 mmol) was dissolved in tetrahydrofurane (THF), triethylamine ($Et_3N$) (5 mL, 35 mmol) and dimethylaminopyridine (DMAP) (30 mg) were added, and the mixture was cooled to 0° C. Then, commercial p-nitrophenyl chloroformate (IVa) (Sigma-Aldrich) (3 g, 15 mmol), dissolved in THF (50 mL), was added dropwise, and the reaction was stirred for 12 h at room temperature. After completion, the reaction was filtered, the solvent was evaporated, and the crude product was digested in a mixture of ethyl acetate and hexane (EtOAc/Hex) to give compound 2 (1.35 g, 90%) in the form of a yellowish solid. The activation of an —OH radical of a molecule with p-nitrophenyl chloroformate (IVa) to give a carbonate is disclosed by Gopin et al., "Enzymatic Activation of Second-Generation Dendritic Prodrugs; Conjugation of Self-Inmolative Dendrimers with Poly (ethylene glycol) via Click Chemistry", *Bioconjugate Chemistry*, 2006, vol. 17, pp. 1432-1440.

1H-NMR (400 MHz, $CDCl_3$): δ=8.33 (d, J=12 Hz, 2H), 8.10 (d, J=8.0 Hz, 1H), 7.65 (t, J=8.0 Hz, 1H), 7.55 (d, J=12 Hz, 2H), 7.40 (t, J=8.0 Hz, 1H), 7.30 (d, J=8.0 Hz, 1H), 3.91 (s, 3H);

A solution of di-tert-butyl dicarbonate (6.1 g, 28 mmol) in dichloromethane was added dropwise to a solution of ethylenediamine (11.2 mL, 166.7 mmol) in dichloromethane (50 mL) with vigorous stirring. Stirring was continued for a further 24 h at room temperature. After concentration to an oily residue, the reaction mixture was dissolved in aqueous sodium carbonate and extracted with dichloromethane. The organic layer was dried (anhydrous $MgSO_4$) and the solvent evaporated under reduced pressure to yield 3 (4.47 g, 100%) as a colourless viscous liquid, corresponding to 1-(t-Butyloxycarbonyl)ethyldiamine (Compound 3). The synthetic route to obtain 1-(t-butyloxycarbonyl)ethyldi-amine is disclosed in the reference of Jensen et al., "Synthesis of Guanidium-Derived Receptor Libraries and Screening for Selective Peptide Receptors in Water", *Chemistry. A European Journal*, 2002, vol. 8, pp. 1300-1309. $^1$H-NMR (400 MHz, $CDCl_3$): δ=4.93 (bs, 1H), 3.15 (m, 2H), 2.51 (t, J=6.0 Hz, 2H), 1.42 (s, 9H), 1.41 (s, 2H);

Compound 2 (5 g, 15.7 mmol) was dissolved in 30 mL of N,N-dimethylformamide (DMF). 1-(t-Butyloxycarbonyl)ethyldiamine (2.5 g, 15.7 mmol) was added. The reaction was stirred at room temperature for 1 h and monitored by Thin Layer Chromatography (TLC). After completion, the solvent was removed under reduced pressure and the crude product was digested in EtOAc. The resulting solid was dissolved in dichloromethane/methanol (DCM/MeOH). To this solution 2 mL of concentrated HCl were added and the mixture was stirred overnight. The solvents were removed and the crude material was digested in EtOAc to yield compound 4 (3.75 g, yield 75%) in the form of a white solid. The addition of 1-(t-butyloxycarbonyl)ethyldiamine for replacing the p-nitrophenylcarbamate of compound 2 is disclosed in Gopin et al (supra).

$^1$H-NMR (400 MHz, DMSO-$d_6$): δ=8.10 (br, 2H), 7.86 (t, 1H), 7.64 (d, J=2.7, 1H), 7.64 (t, J=7.0 Hz, 1H), 7.37 (t, J=7.0 Hz, 1H), 7.24 (d, J=7.0 Hz, 1H), 3.80 (s, 3H), 3.35 (br, 2H), 2.92 (br, 2H);

1.5 g of compound 4 were dissolved in 25 mL of MeOH and neutralized with sodium hydrogen carbonate. The resulting solution was dried with $MgSO_4$, filtered and evaporated at reduced pressure, to yield the salicylate blocking agent (Ib)

Example 2

Preparation of a Compound of Formula (I) Derived from Methyl Salicylate with Amine Functionality (Compound 1c)

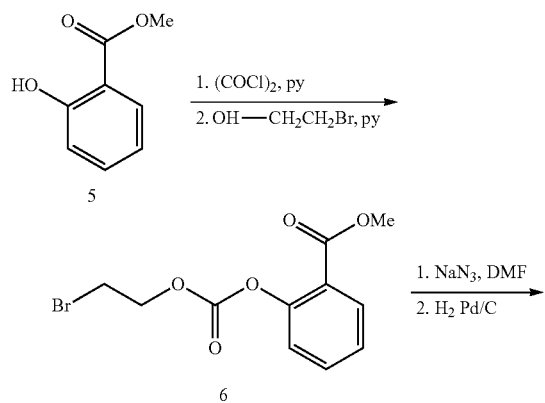

-continued

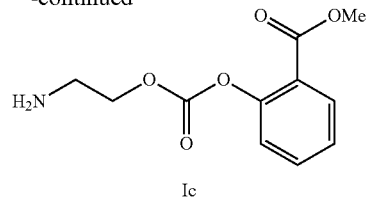

Me: methyl 2.1 g (10 mmol) of methoxycarbonylphenyl chloroformate (prepared according to WO 98/25938) and 60 mL of pyridine were dissolved in toluene. Then, 1.3 g (10 mmol) of 2-bromoethanol were added dropwise with stirring at 0° C. The resulting solution was stirred for 12 h at room temperature. The solvent was evaporated under reduced pressure and the residue was dissolved in dichloromethane. The organic solution was washed with water, dried over $MgSO_4$ and the solvent was removed in vacuo to afford compound 6 (2.5 g, yield 84%). $^1$H-NMR (400 MHz, $CDCl_3$): δ=8.43 (d, J=8 Hz, 1H), 8.10 (t, J=8.0 Hz, 1H), 6.98 (d, J=8.0 Hz, 1H), 6.88 (t, J=8 Hz, 2H), 5.24 (bs, 2H), 4.46 (t, J=8.0 Hz, 2H), 3.96 (s, 3H), 3.64 (t, J=8.0 Hz, 2H).

8.8 g (29 mmol) of methyl 2-((2-bromoethoxy)carbonyloxy)benzoate 6 were dissolved in DMF. Then, 2.3 g (35 mmol) of sodium azide were added at 0° C. and the suspension was stirred at room temperature overnight. The resulting mixture was filtered and the solvent was removed in vacuo. The crude was dissolved in 50 mL of ethyl acetate and hydrogenated at atmospheric pressure in the presence of 1 g of Pd/C 10% overnight. Then, the catalyst was filtered off and the solvent was removed to yield compound 1s (5.1 g, yield 74%). $^1$H-NMR (400 MHz, $CDCl_3$): δ=7.83 (d, J=8 Hz, 1H), 7.45 (t, J=8.0 Hz, 1H), 6.98 (d, J=8.0 Hz, 1H), 6.88 (d, J=8 Hz, 1H), 5.26 (bs, 2H), 4.44 (t, J=8.0 Hz, 2H), 3.94 (s, 3H), 3.65 (t, J=8.0 Hz, 2H).

Example 3

Preparation of the Compound of Formula (Ic) Derived from Tranilast

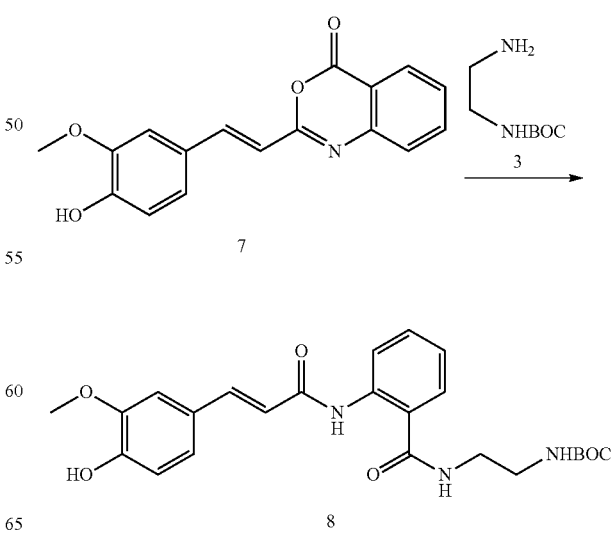

Compound 7 (1.46 g, 4.9 mmol synthesized according to Brett et al., "Avenanthramides in Oats (*Avena sativa* L.) and Structure—Antioxidant Activity Relationships" *J. Aqric. Food Chem,* 2003, vol. 51 (3), pp. 594-600) was dissolved in dimethylformamide (DMF) and 1.2 g of the amine 3 (7.4 mmol) were added, and the mixture was stirred overnight at room temperature. After completion, the reaction was filtered, the solvent was evaporated, and the crude product was digested in a mixture of ethyl acetate and hexane to give compound 8 (2.0 g, yield 89%) in the form of a yellowish solid. $^1$H-NMR (400 MHz, CDCl$_3$): δ=11.36 (s, 1H), 8.78 (d, J=8.0 Hz, 1H), 7.67 (d, J=16 Hz, 1H), 7.61 (m, 2H), 7.49 (m, 1H), 7.09 (m, 2H), 7.93 (d, J=8.0 Hz, 1H), 6.46 (d, J=16 Hz, 1H), 5.02 (brs, 1H), 3.95 (s, 3H), 3.54 (m, 2H), 3.46 (m, 2H), 1.53 (s, 9H).

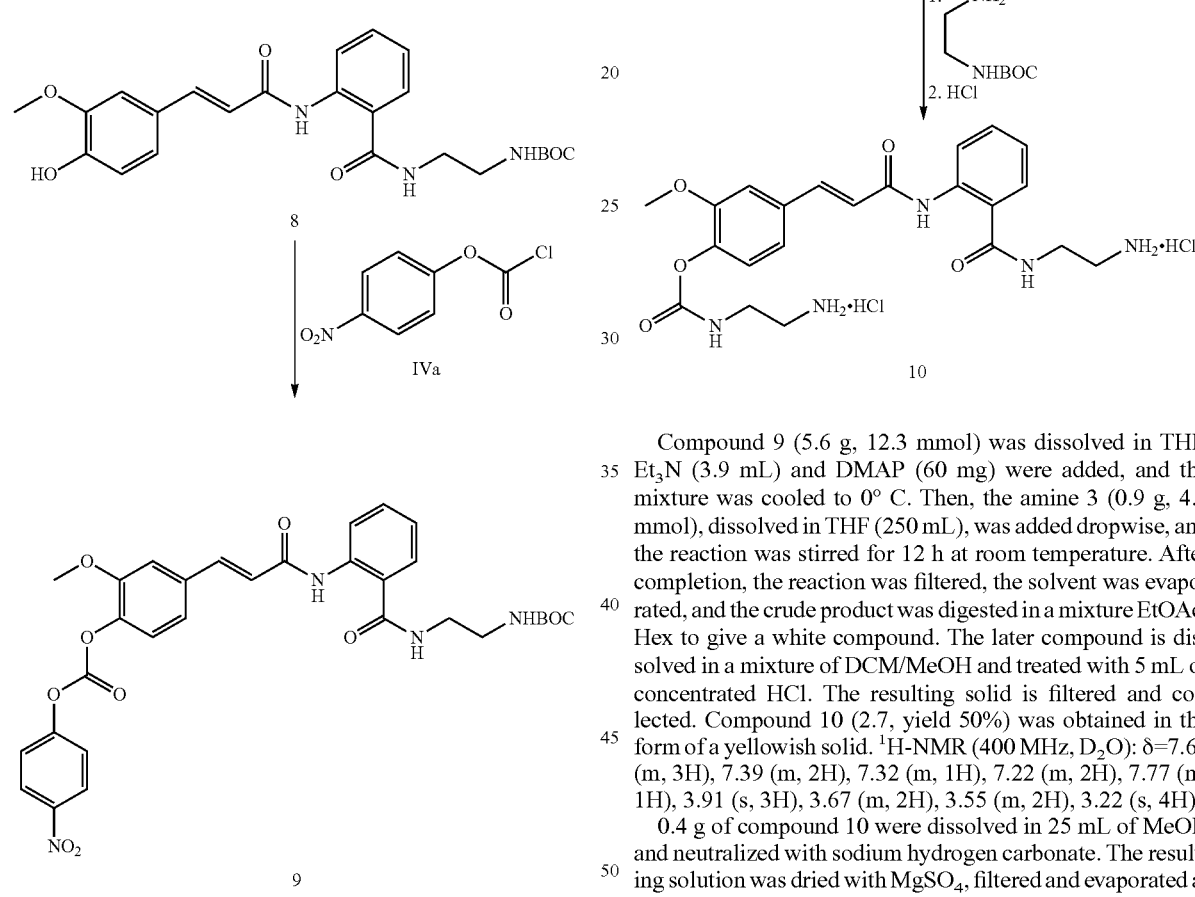

compound 8 (5.6 g, 12.3 mmol) was dissolved in THF, Et$_3$N (3.9 mL) and DMAP (60 mg) were added, and the mixture was cooled to 0° C. Then, p-nitrophenyl chloroformate (2.7 g, 13.4 mmol) (IVa) was introduced and the resulting mixture was stirred for 12 h at room temperature. After completion, the reaction was filtered and the solvent was evaporated. The crude product was digested in a mixture EtOAc/Hex to give compound 9 (7.2 g, yield 94%) in the form of a white solid. $^1$H-NMR (400 MHz, CDCl$_3$): δ=11.78 (s, 1H), 8.70 (d, J=8.0 Hz, 1H), 8.18 (d, J=8 Hz, 2H), 7.67 (d, J=16 Hz, 1H), 7.61 (m, 2H), 7.49 (m, 1H), 7.16 (m, 1H), 7.09 (m, 1H), 7.93 (d, J=8.0 Hz, 1H), 6.91 (d, J=8 Hz, 2H), 6.46 (d, J=16 Hz, 1H), 5.02 (brs, 1H), 3.95 (s, 3H), 3.54 (m, 2H), 3.46 (m, 2H), 1.47 (s, 9H).

Compound 9 (5.6 g, 12.3 mmol) was dissolved in THF, Et$_3$N (3.9 mL) and DMAP (60 mg) were added, and the mixture was cooled to 0° C. Then, the amine 3 (0.9 g, 4.5 mmol), dissolved in THF (250 mL), was added dropwise, and the reaction was stirred for 12 h at room temperature. After completion, the reaction was filtered, the solvent was evaporated, and the crude product was digested in a mixture EtOAc/Hex to give a white compound. The later compound is dissolved in a mixture of DCM/MeOH and treated with 5 mL of concentrated HCl. The resulting solid is filtered and collected. Compound 10 (2.7, yield 50%) was obtained in the form of a yellowish solid. $^1$H-NMR (400 MHz, D$_2$O): δ=7.62 (m, 3H), 7.39 (m, 2H), 7.32 (m, 1H), 7.22 (m, 2H), 7.77 (m, 1H), 3.91 (s, 3H), 3.67 (m, 2H), 3.55 (m, 2H), 3.22 (s, 4H).

0.4 g of compound 10 were dissolved in 25 mL of MeOH and neutralized with sodium hydrogen carbonate. The resulting solution was dried with MgSO$_4$, filtered and evaporated at reduced pressure to yield the tranilast chain extender (Id)

Example 4

Preparation of the Compound of Formula (Ie) Derived from Naproxen

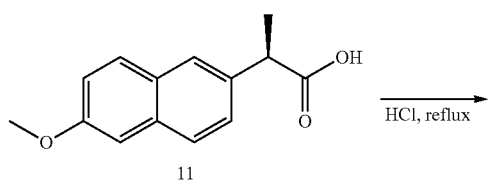

-continued

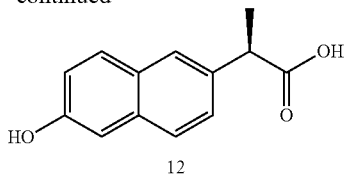

12

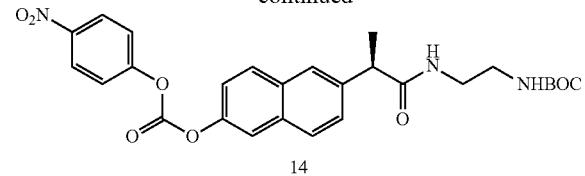

14

12 g of Naproxen 11 were suspended in 200 mL of HCl 20% and refluxed for 48 hours (h). The resulting slurry was filtered and the residue was washed with water (3×50 mL). The solid collected was dried under vacuum. Compound 12 was obtained as an off white solid (10.7 g, 95% of yield). $^1$H-NMR (400 MHz, DMSO-d$_6$): δ=10.74 (brs, 1H), 8.58 (s, 1H), 7.76 (d, J=8 Hz, 1H), 7.72 (s, 1H). 7.67 (d, J=8 Hz, 1H), 7.76 (dd, J=8 Hz, J=4 Hz, 1H), 7.19 (m, 1H), 7.14 (dd, J=8 Hz, J=4 Hz, 1H), 3.55 (m, 1H), 1.52 (d, J=8 Hz, 3H).

Compound 13, (14.2 g, 40 mmol) was dissolved in THF, Et$_3$N (40 mL) and DMAP (150 mg) were added, and the mixture was cooled to 0° C. Then, p-nitrophenyl chloroformate (8.1 g, 40 mmol) (IVa), dissolved in THF, was added dropwise, and the reaction was stirred at room temperature. After completion, the reaction was filtered, the solvent was evaporated, and the crude product was digested in a mixture of EtOAc/Hex (1:1) to give compound 14 (19.4 g, yield 94%) in the form of a yellowish solid.

$^1$H-NMR (400 MHz, CDCl$_3$): δ=8.33 (d, J=8 Hz, 2H), 7.88 (d, J=8 Hz, 2H), 7.83 (d, J=8 Hz, 2H), 7.79 (2, 1H), 7.73 (d, J=4 Hz, 1H), 7.52 (d, J=8 Hz, 2H), 7.51 (m, 1H), 7.40 (dd, J=8 Hz, J=4 Hz 1H), 6.26 (brs, 1H), 4.52 (brs, 1H), 3.72 (m, 1H), 3.36-3.21 (3, 4H), 1.55 (d, J=8 Hz, 3H), 1.37 (s, 9H).

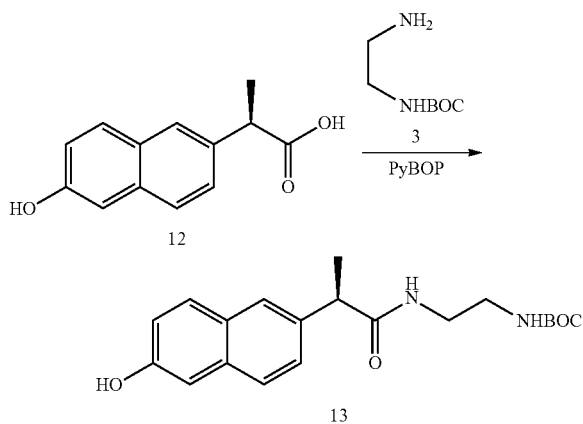

Acid 12 (0.8 g, 3.7 mmol) and PyBOP (1.9 g, 3.7 mmol), were suspended in 20 mL of DCM at 0° C. under atmosphere of nitrogen. Then 2.6 mL of DIPEA were added. Once all the solids were dissolved a solution of 1-(t-butyloxycarbonyl) ethyldiamine 3 (0.6 g, 3.7 mmol) in 20 mL of DCM was added. The mixture was stirred overnight and monitored by TLC. After completion of the reaction, the solvent was removed under reduced pressure. The crude product was purified by column chromatography on silica gel (EtOAc:Hex) to give compound 13. $^1$H-NMR (400 MHz, CDCl$_3$): δ=7.71 (brs, 1H), 7.56 (s, 1H), 7.53 (m, 1H), 7.48 (m, 1H), 7.27 (m, 1H), 7.04 (m, 2H), 6.40 (brs, 1H), 5.01 (brs, 1H), 3.30 (m, 2H), 3.15 (m, 2H), 1.55 (d, J=8 Hz, 3H), 1.40 (s, 1H).

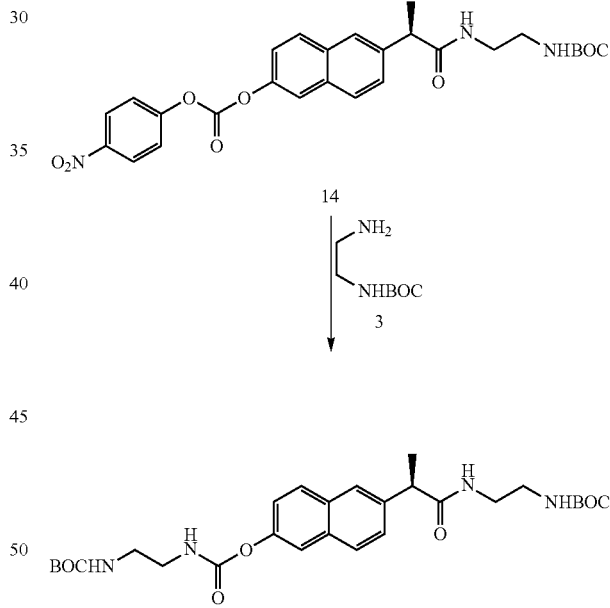

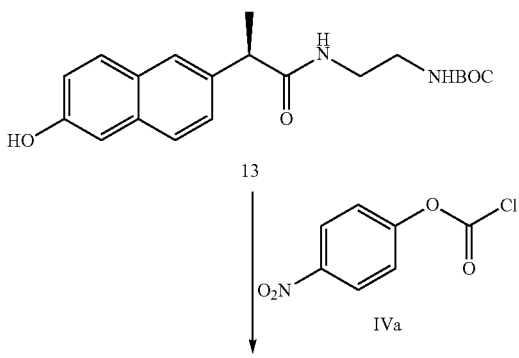

Compound 14 (10 g, 19.1 mmol) was dissolved in DMF. 1-(t-butyloxycarbonyl)ethyldiamine 3 (4 g, 24.9 mmol) was added. The reaction was stirred at room temperature for 1 h and monitored by TLC. After completion, the solvent was removed under reducted pressure and the crude product was digested in EtOAc to give after filtration and drying under vacuum 6.1 g of compound 15 (yield 67%). $^1$H-NMR (400 MHz, DMSO-d$_6$): δ=8.00 (brs, 1H), 7.88 (d, J=8 Hz, 1H), 8.33 (d, J=8 Hz, 2H), 7.79 (m, 2H), 7.57 (m, 1H), 7.48 (d, J=8 Hz, 1H), 7.26 (d, J=8 Hz, J=4 Hz 1H), 6.90 (brs, 1H), 6.75 (brs, 1H), 3.73 (m, 1H), 3.10-2.94 (m, 8H), 1.40 (d, J=8 Hz, 3H), 1.39 (s, 9H), 1.35 (s, 9H).

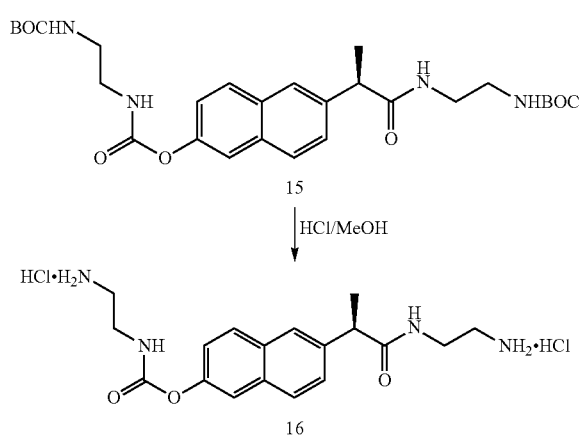

MeOH: methanol 6.1 g of compound 15 was dissolved in a 1:1 mixture of DCM/MeOH (1 L). To this solution 2 mL of concentrated HCl were added and the mixture was stirred overnight. The solvents were removed and the crude material was digested in EtOAc to yield compound 16 (4.3 g, yield 95%). $^1$H-NMR (400 MHz, D$_2$O): δ=7.95 (d, J=8 Hz, 1H), 7.92 (d, J=8 Hz, 1H), 7.91 (s, 1H), 7.57 (m, 1H), 7.67 (m, 1H), 7.54 (d, J=8 Hz, 1H), 7.37 (d, J=8 Hz, J=4, 1H), 3.98 (m, 1H), 3.59-3.36 (m, 4H), 3.24 (m, 2H), 3.12 (m, 2H), 1.59 (d, J=8 Hz, 3H).

ATR-FTIR (v/cm$^{-1}$): 3332, 2889, 2752, 2486, 2024, 1705, 1656, 1604, 1529, 1504, 1476, 1445, 1341, 1262, 1239, 1173, 1162, 1138, 1116, 949, 933, 888, 878, 819, 780, 667.

1.5 g of compound 16 were dissolved in MeOH and neutralized with sodium hydrogen carbonate. The resulting solution was dried with MgSO$_4$, filtered and evaporated at reduced pressure to yield the naproxen chain extender (Ie).

ATR-FTIR (v/cm$^{-1}$): 3285, 3060, 2972, 2935, 2876, 1722, 1651, 1545, 1504, 1475, 1217, 1153, 947, 892, 816.

Example 5

Preparation of the Polyurethanes 5.1. Synthesis of the Prepolymer (Polyurethane Compound):
Raw Materials
poly(1,6-hexacarbonate)diol (from UBE Eternacoll UH-100) vacuum dried for 4 hours at 80° C.;
polydimethylsiloxanediol (PDMS) (from Shin Etsu X22-160AS) vacuum dried for 15 hours a 105° C.

In a 250 mL capacity reactor provided with a mechanical agitator, a nitrogen atmosphere, and a thermometer 76 g of pure MDI were melted at 60° C. While maintaining the temperature, 122.8 g of poly(1,6-hexacarbonate)diol (UBE UH-100) and 30.7 g of polydimethylsiloxanediol (Shin-Etsu X22-160AS) were added dropwise through an addition funnel. After 40 minutes the addition was stopped and the mixture was stirred at 60° C. while adjusting the viscosity with MEK. After 60 minutes an NCO index of 4.13 mg NCO/g was obtained. The white resin so obtained (Prepolymer=PREPO) was recovered and kept under nitrogen atmosphere.

The methanolic carbamate of the prepolymer was characterized using GPC. The data derived from the GPC are listed in Table 1 below, wherein it can be seen that the prepolymer had an average molecular weight (Mw) of 5936 Da. Table 1 also shows the number average molecular weight (Mn), the weight average molecular weight (Mw), the Z average molecular weight (Mz) and the molecular weight distribution (D):

TABLE 1

| | |
|---|---|
| Mn | 3207 Da |
| Mw | 5936 Da |
| Mz | 10456 Da |
| D | 1.8512 |

5.2. Polyurethane Synthesis:
Polyurethane polymer containing naproxen (PU-NAP):
To 11.40 g of the prepolymer (PREPO) (See 5.1), 3.5 g of the diamine compound Ie (see example 4), and 57 g of DMF were added. The mixture was stirred for 15 minutes at room temperature (18° C. to 32° C.). The mixture was added over 740 mL of MeOH, and washed 3 times with 100 mL deionized water at room temperature. Then the mixture was washed with water and MeOH. 12.5 g of the white polymer so obtained were dissolved in a mixture of MEK/DMF (1:2.6) to adjust the viscosity. The polymer was applied with an extender of 500 μm. The film so obtained was cured for 24 h at 80° C. in a furnace. $^1$H-NMR (400 MHz, DMSO): b=9.67-9.48 (m, 5H), 8.68 (s, 1H), 7.99-7.83 (m, 5H), 7.34 (m, 4H), 7.08 (m, 4H), 4.02 (m, 24H), 3.78 (s, 2H), 3.51 (s, 8H), 1.57 (s, 28H), 1.30 (s, 28H) 0.04 (s, 11H);

Polyurethane polymer containing tranilast (PU-TRAN):
To 4.3 g of the prepolymer (PREPO) (See 5.1), 1.63 g of the diamine compound Id (see example 3), and 22.82 g of DMF were added. The mixture was stirred for 15 minutes at room temperature (18° C. to 32° C.). The mixture was added over MeOH, and washed with deionized water and MeOH. 3.0 g of the yellow polymer so obtained were dissolved in 3 g of a mixture of MEK/DMF (1:2, 6). The polymer was applied with an extender of 500 μm. The film so obtained was cured for 24 h at 80° C. in a furnace. $^1$H-NMR (400 MHz, DMSO-d$_6$): δ=9.51 (s, 5H), 8.63-8.51 (m, 4H), 7.39 (m, 4H), 7.12 (m, 4H), 6.83 (s, 1H), 6.53 (s, 1H) 4.09 (m, 28H,), 3.87 (s, 2H), 3.51 (s, 8H), 1.61 (s, 28H), 1.34 (s, 28H), 0.04 (s, 11H);

Polyurethane polymer containing methyl salycilate (PU-SAL):
To 22.5 g of the prepolymer (PREPO) (See 5.1), 4.5 g of the diamine compound derived from methyl salycilate of formula Ic (see example 1), and 100 g of DMF were added. The mixture was stirred for 15 minutes at room temperature (18° C. to 32° C.). The mixture was added over MeOH, and washed with deionized water and MeOH. 20.7 g of the yellow polymer so obtained were dissolved in 60.7 g of a mixture of MEK/DMF (1:2, 6). The polymer was applied with an extender of 500 μm. The film so obtained was cured for 24 h at 80° C. in a furnace. $^1$H-NMR (400 MHz, DMSO-d$_6$): δ=9.47 (s, 1H), 8.51 (s, 1H) 7.94 (m, 1H), 7.44 (m, 1H), 7.33 (m, 4H), 7.18 (m, 2H), 7.04 (m, 4H), 4.05 (m, 4H,), 3.83 (s, 2H), 3.48 (m, 8H), 1.57 (s, 12H), 1.30 (s, 14H), 0.04 (s, 5H);

All these polyurethane polymers have the compounds of formula (I) embedded into the backbone. The compounds of formula (I) are thus suitable for extending the polyurethane chain, when compounds such as those of formula (Ie) and (Id) are employed, or they are suitable compounds for terminating the polyurethane reaction, when compounds of formula (Ib) or (Ic) are employed.

Polyurethane polymer containing 1,4-butanediol (PU-BD) (Comparative polymer):
23.44 g of the prepolymer (PREPO) (See 5.1) were weighted in a polypropylene recipient, and 1.56 g of the 1,4-butandiol were added. The mixture was vigorously stirred for 15 minutes, and trespassed to an aluminum capsule. The film so obtained was cured for 24 h at 80° C. in a furnace. 21.3 g of the white polymer so obtained in a weight percent of (26%) were dissolved in a mixture of MEK/DMF (1:2, 6).

The polymer was washed MeOH. The polymer was re-dissolved in a mixture of MEK:DMF (1:2, 6) and it was applied with a film extender of 500 μm. The film so obtained was cured for 24 h at 80° C. in a furnace. $^1$H-NMR (400 MHz, DMSO-d$_6$): δ=9.48 (d, 2H, J=10), 7.34 (d, 4H, J=8.3), 7.07 (d, 4H, J=8.1), 4.03 (m, 11H), 3.77 (s, 2H), 3.32 (s, 8H), 1.69 (s, 2H), 1.56 (s, 10H), 1.30 (s, 10H), 0.04 (s, 6H);

TABLE 2

Mechanical properties of the polyurethanes of Example 5 according to UNE 53-510-85 (DIN 53-504)/MPa.

| PROPERTIES | PU-BD (Comparative) | PU-NAP |
|---|---|---|
| Mod. 50% | 7.2 | 8.1 |
| Mod. 100% | 9.0 | 9.1 |
| Mod. 200% | 14.6 | 12.9 |

Mod. 50%, 100% and 200% are the tensions measured at 50%, 100% and 200% deformation respectively.

From Table 2 it can be seen that the mechanical properties of the polyurethanes containing in the backbone the compound of formula (Ie), which is derived from naproxen (PU-NAP), are similar to the properties of a similar polyurethane containing BD (PU-BD) (Comparative).

Example 6

Cytotoxicity Data

In order to prove that the polyurethanes of the invention, comprising in their backbone a compound of formula (I) derived from a substance which has anti-inflammatory, analgesic and/or anti-proliferative properties, were able to be inserted into an animal or human body, the following tests were performed to determine if they could be hazard for the health. Thus, the cytotoxicity of the polyurethanes was evaluated by determining if the normal growth of an established cell line is affected by the presence of the polyurethane polymers of the invention.

The method for determining the cytotoxicity of the polymers was that disclosed in the Standard UNE EN ISO 10993-5, "Biological evaluation of biomedical products: In vitro cytotoxicity assays", by means of which the cytotoxicity is indirectly determined Sample Preparation:

The samples tested were prepared as films with a thickness lower than 5 mm. The extraction ratio was of 6 cm$^2$/ml for the tested and control samples. The control samples are polyvinilchloride-tin (PVC-Sn) as positive controls for cytotoxicity, and high density polyethylene (PE) as negative control.

All the samples were extracted with the cell culture MEM (Eagle's Minimum Essentials Medium). Another control is the test of the control media (media without sample)

The tubes were extracted for 24 h at 37° C. and in at atmosphere of 5% CO$_2$, thus representing a short-period contact with the body. The films were extracted for 24 h, 48 h and 72 h at 37° C. and in at atmosphere of 5% CO$_2$, thus representing a long-period contact with the body.

The tests is performed with the cell line CCL-171, corresponding to lung human fibroblasts. The cells are cultured in MEM (Eagle's Minimum Essentials Medium) with 10% of fetal bovine serum (FBS) and 1% of antibiotic/antimycotic agent. The day before the test 5000 cells were seeded in each well with complete MEM (10% FBS).

The extracts were contacted with the cells by previously removing the cell media of each well of the plate. All the samples were tested at least in triplicate. After 24 hours the cell viability was measured. The cell media was removed and 100 μl of MEM and 10 μl of the compound WST-1 were added in each well. WST-1 is a compound metabolized by the mitochondria of alive cells and its metabolite, formazan, can be measured by spectroscopy at a wave-length of 450 nm. In this test, the absorbance is equivalent to the metabolic activity of the cells, that is, to the viability of the cells. Once the WS-T1 was added, the wells were incubated for 4 hours at 37° C., and finally the absorbance was measured in an ELISA plate lector at 450 nm.

The cell viability of the extracts from extractions of 24 h, 48 h and 72 h was determined using the following formula:

$$\text{Cell viability }(\%) = \frac{\text{Test sample absorbance}}{\text{Control sample absorbance}} \times 100$$

In this formula it is assumed that the cells in contact with the control media represent the 100% of viability, in such a way that the results are compared with the viability of the cells in contact with this control media. t-Student is used for the statistical study and a p<0.05 is considered as statistical significance. Viability is the contrary to cytotoxicity. The Standard UNE EN ISO 10993 considers that a material is cytotoxic if the viability is lower than 70%, that is, if the toxicity is greater than 30%.

In Table 3 below, the cytotoxicity data are listed. The values represent the mean of at least 3 replicates of every test.

TABLE 3

Cytotoxicity assay according to UNE EN ISO 10993-5

| | PU-BD (Comparative) | PU-NAP | PU-TRAN |
|---|---|---|---|
| % viability at 24 h | 100 | 90 | 105 |
| % viability at 48 h | 95 | 110 | 95 |
| % viability at 72 h | 100 | 120 | 100 |

As deductible from Table 3, all the polyurethane polymers of the invention allow the cells to grow, thus representing non-cytotoxic materials.

Example 7

Platelet Adhesion Associated to the Polyurethane Compounds of the Invention

In order to detect if the polymers of the invention could promote the proliferation or aggregation of cells, it was determined if the human platelets were able to adhere onto the surface of the polymer, thus helping to promote thrombosis, an event which should be avoided or at least minimized.

Platelets have a normal blood concentration of 140–450×10$^9$ platelets/L with a size of 2-3 μm. The source of platelets for this study was plasma from volunteers' blood donors. The platelets were suspended in the storage solution for platelets (SPP+). For the study the platelets were suspended in a cell media RPMI 1640 (SIGMA) supplemented by antibiotic/antimycotic (from GIBCO).

A dilution of the plasma containing the platelets was done in the cell culture media. Films of PU-BD (Comparative), PU-NAP and PU-TRAN as those of the example 6 were disposed into culture plaques and 100 μl of the dilution of the platelets were added. The mixture was incubated for 3 hours at 37° C. and afterwards the number of cells adhered to the different films was spectroscopically determined (n=5), as well as observed by means of an optical microscope (n=2).

For the spectroscopic analysis, the samples were treated with Phosphate Buffer Saline (PBS) to wash the platelets not adhered to the films. The number of adhered cells was evaluated with the commercial kit Cytotoxicity Detection Kit (LDH. ROCHE), which detects the Lactate dehydrogenase activity (LDH) from the cells, previously lysed with a lysis buffer (Triton-X100 in PBS), by determination of the absorbance at 490 nm. The number of adhered cells is calculated considering as the 100% of adhesion the absorbance detected for the initial platelet concentration added to the samples. As negative control a film with high density polyethylene is employed. FIG. 1 shows the platelet adhesion (%) observed. The percentages are low and similar in all the samples, and concordant with the percentage of the negative control (PE).

The samples are then washed and stored (4° C.), or visualized in a Scanning Electronic Microscope (SEM) or in an optical microscope. As a negative control a sample of each film without platelet incubation was used, and a collagen coating (Becton Dickison) was used as a positive control of cell adhesion.

The platelet adhesion ranges for the positive control and for the samples, observed means of the enzymatic assay (FIG. 1) or using SEM (data not shown) clearly indicate that the adhesion is very low, and similar to those of the negative control (PE). Hence, it is to be considered that the platelet adhesion is negative. It must be ascertained that patient variability can be observed regarding the platelet concentration in plasma that can lead to worth variability in the observed results if different platelet batches are analysed.

Example 8

Determination of the Pro-Inflammatory Effect of the Polyurethanes of the Invention The films of polyurethane (PU-TRAN, and PU-NAP of Example 5.2) obtained with the compounds of formula (Ie) and (Id) of Examples 3 and 4, respectively, were tested to determine if they promoted the expression and/or secretion of inflammatory compounds in a cell culture derived from HUVEC cells (ATCC: CRL-1730), derived from human umbilical vein endothelial cells. The test was also performed with a film made of polyurethane containing 1,4-butanediol (PU-BD of Example 5.2, as comparative polymer). 5-6 replicates were performed for each tested material.

After contacting the cells with the above-mentioned films for 48 hours, it was firstly detected that the cell viability was greater than the 80%, as indicated in Example 6. Then the levels of pro-inflammatory markers or compounds was analysed.

The studied pro-inflammatory markers were: Vascular Cell Adhesion Molecule-1 (VCAM-1), E-selectin, and Interleukin 8 (IL-8). The positive control was a HUVEC cell culture in which the inflammatory state had been induced. The negative control was the HUVEC cell culture not being in contact with the polyurethane films.

The detection of E-selectin and VCAM was performed by Fluorescence-activated Cell Sorting in a FASCalibur Becton Dickinson Cytometer. The markers were detected on the cell surface with fluorescent-conjugated antibodies. For E-selectin it was used the Phycoeritrin (PE) conjugated mouse Anti-Human CD62E (Becton Dickinson 55145) and the Phycoeritrin (PE) conjugated mouse IgG1, k Isotype Control (Becton Dickinson 555749). For VCAM-1 it was used the Alophycocianin (APC) conjugated mouse Anti-Human CD106 (Becton Dickinson 55147) and the APC conjugated mouse IgG1, k Isotype Control (Becton Dickinson 555751).

The detection of IL-8 was performed by detecting from the supernatant of the cell cultures the soluble IL-8 protein using the fluorescence sphere technology (CBA). The spheres containing the antibody anti-IL-8 were contacted with the supernatant. The kits and reagents to perform the analysis of IL-8 were the Human IL-8 Flex Set (Becton Dickinson 558277) and the Human Soluble Protein Master Buffer Kit (Becton Dickinson 558264).

Table 4 below illustrates the results obtained with the above-mentioned assays.

TABLE 4

Detection of pro-inflammatory markers in HUVEC cells.
Pro-inflammatory markers

| Marker | E-Selectin | | VCAM-1 | | IL-8 | |
|---|---|---|---|---|---|---|
| Sample | Int. FI | SD | Int. FI | SD | CC(pg/ml) | SD |
| HUVEC | 14.00 | 0.74 | 9.91 | 0.29 | 693 | 80 |
| HUVEC* | 18.11 | 0.42 | 19.27 | 2.17 | 39178 | 1019 |
| PU-BD Comparative | 13.45 | 0.60 | 12.95 | 2.69 | 103 | 4 |
| PU-NAP | 13.31 | 0.39 | 11.38 | 1.14 | 190 | 71 |
| PU-TRAN | 13.74 | 0.46 | 12.27 | 2.62 | 306 | 148 |

HUVEC*: positive control. Int. FI: Fluorescence Intensity. SD: Standard deviation. CC: Concentration.

As deduced from Table 4, all the samples give signals similar to those of the negative control (HUVEC cell without films and without induced inflammation). Hence, it can be affirmed that the materials do not provoke any inflammatory effect, and that the inflammatory percentage is null.

These results show that these materials can be used for the manufacturing of devices which have to be implanted or in contact with the inner of the body, since they will not activate an inflammatory reaction leading to a painful and unfeasible experience for a patient contacted with such a devices.

Example 9

Determination of the Anti-Inflammatory Effect of the Polyurethanes of the Invention A film of polyurethane (PU-NAP of Example 5.2) obtained with the compound of formula (Ie) of Examples 4, was tested to determine if it could infer an anti-inflammatory effect to a cell culture derived from HUVEC cells (ATCC: CRL-1730), derived from human umbilical vein endothelial cells. The film of PU-NAP conformed a coating on a polystyrene well-plate (6-well/plate)

The assay wanted to determine if the polymers of the invention are able to reduce the level of some cell inflammatory markers (proteins which are over-expressed in an inflammatory state).

A monolayer of HUVEC cells seeded in a film of PU-NAP were contacted with a pro-inflammatory agent, the alfa tumoral necrosis factor (TNF-α). The TNF incubation was of 18 hours, thus the cells were in contact with the PU-NAP film for 48 hours. As negative control HUVEC cells were seeded in wells coated with PU-NAP, and they were incubated with the cell medium without TNF. The positive control was a HUVEC cell culture in which the inflammatory state had been induced in contact with the TNF but in absence of the PU-NAP. 5-6 replicates were performed for each tested material and control.

Firstly, the cell viability was detected as in Example 6 in order to see that it was greater than the 70%. Secondly, the levels of inflammatory markers or compounds were analysed.

The studied inflammatory markers were the same of Example 8: Vascular Cell Adhesion Molecule-1 (VCAM-1), E-selectin, and Interleukin 8 (IL-8). The detection of E-selectin, VCAM and IL-8 was performed as in Example 8.

Table 5 below illustrates the results obtained with the above-mentioned assays.

TABLE 5

Detection of pro-inflammatory markers in HUVEC cells.
Anti-inflammatory markers

| Marker | E-Selectin | | VCAM-1 | | IL-8 | |
|---|---|---|---|---|---|---|
| Sample | Int. FI | SD | Int. FI | SD | CC(pg/ml) | SD |
| HUVEC | 14.00 | 0.74 | 9.91 | 0.29 | 693 | 80 |
| HUVEC* | 18.11 | 0.42 | 19.27 | 2.17 | 39178 | 1019 |
| PU-NAP | 16.12 | 1.08 | 14.86 | 1.40 | 11438 | 2192 |

HUVEC*: positive control. Int. FI: Fluorescence Intensity. SD: Standard deviation. CC: Concentration.

Moreover, the percentage of inhibition of inflammatory markers (anti-inflammatory effect) was calculated according to the following formula:

$$\text{Marker inhibition}(\%) = \frac{HUVEC^* - PU\text{-}NAP \times 100}{HUVEC^* - HUVEC}$$

In Table 6, the inhibition (%) for each inflammatory marker is indicated.

TABLE 6

| | Marker inhibition (%) | | |
|---|---|---|---|
| Marker | E-Selectin | VCAM-1 | IL-8 |
| % | 48.42 | 47.12 | 72.08 |

As deduced from Tables 5 and 6, it can be seen that due to the presence of PU-NAP the concentration of inflammatory markers was reduced in respect of the positive control (HUVEC*). A higher percentage of inhibition was observed for IL-8 (72.08%).

Thus, it can be affirmed that the PU-NAP of Example 5.2 produced an anti-inflammatory effect in vitro.

These results reinforce the use of the polymeric materials of the invention for the manufacturing of devices which have to be implanted or in contact with the inner of the body. In fact, these materials not only do not activate an inflammatory reaction, but they act as anti-inflammatory agents too. It is therefore advantageous its use, since they can infer a therapeutic or prophylactic effect when placed into a selected body region.

Example 10

Stability of the Polyurethanes of the Invention

The stability of the polyurethanes of the invention was evaluated to elucidate if the same remained intact when submitted to extreme conditions. The extreme conditions intended to reproduce in a short period of time the real situation of a device implanted in the body of a human patient or other non-human animal. The stability test was performed by submitting the polyurethanes of the invention to an accelerated oxidative degradation.

Accelerated Oxidative Degradation:

Following the standard according to UNE EN ISO 10993-12 (Biologic evaluation of sanitary products. Sample preparation and reference materials) and UNE EN ISO 10993-13 (Biologic evaluation of sanitary products Identification and quantitative determination of the degradation products of the biomedical sanitary products) a ratio of sample/oxidative solution of 1:40 (w/v) was used in order that all the samples be covered by the solution. Rectangular polyurethane films of Example 5.2 containing naproxen (PU-NAP) (n=3) and with a weight of 0.1 g, were rolled and disposed in assay tubes (borosilicate 13×100 mm tube with PTFE caps). The tubes contained 4 mL of an oxidative solution. The oxidative solution comprised 20% $H_2O_2$ (Panreac, ref: 131077) in $CoCl_2$ (Sigma-Aldrich, 97%, ref: 232696) in a concentration of 0.1M. The samples were contacted with the solution at 37° C. and stirred in an orbital stirrer at 125 rpm, under sterile conditions. Incubation times were 0 (control), 1 month, and 2 months (the solution was changed every 3.5 days).

Once the incubation time was finished, the samples were washed with deionised water in a Petri plaque and dried in vacuum for 1 week.

The polyurethane film comprising the compound of formula (Ie) (PU-NAP) was characterized by Attenuated Total Reflectance-Infrared Spectroscopy (ATR-IR) using a Nicolet 6700 FT-IR Spectrometer provided with Smart OMNI-Sampler.

Figure 2:
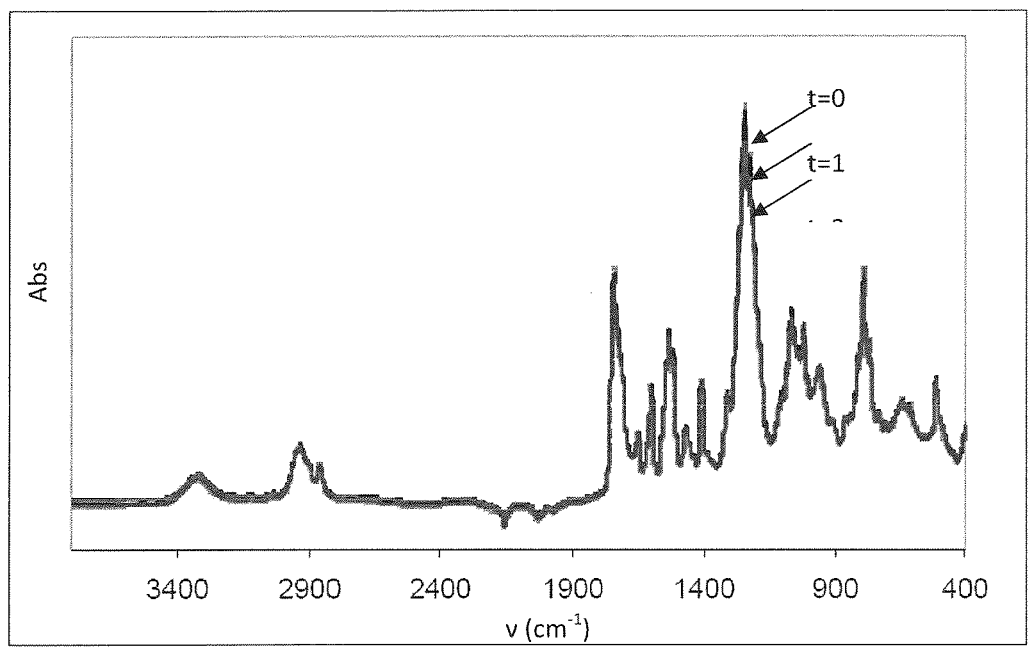
FIG. 2, relating to Example 10, shows an IR spectra of a polyurethane according to the invention (PU-NAP, see example 5.2) at time 0 (control; C) and at times 1 (t=1) and 2 (t=2) months after being submitted to an accelerated oxidative degradation. The spectra were obtained by means of ATR-FTIR in a Nicolet 6700 FT-IR Spectrometer provided with Smart OMNI-Sampler using the surface probe. The X-axis indicates the frequency (v) in cm$^{-1}$ and the Y-axis represents the absorbance (Abs).

FIG. 2 show the collected data with an incubation time of 0 (control), of 1 month and 2 months. As can be seen, the IR spectra at different times are totally overlapped.

All these data allow concluding that the polymers with the compounds of formula (I) of the invention are resistant to extreme environments and that they are suitable to resist for a long period in the environment of the inner of a body, in which a great proportion of water is present, and in which enzymatic reactions broadly occur.

Example 11

Stents with Polyurethanes of the Invention

Figure 3:
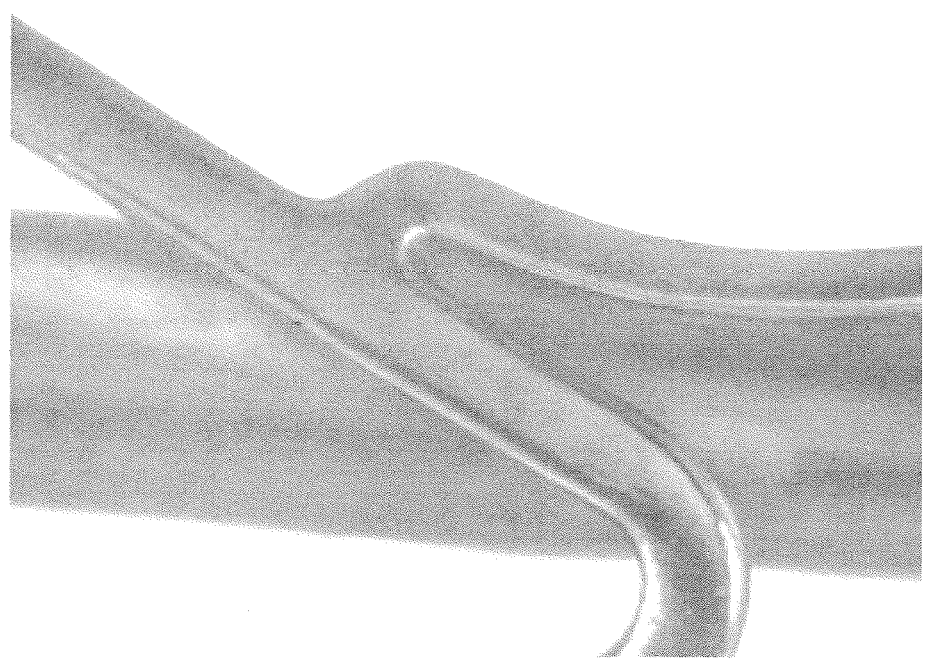
FIG. 3 relating to example 11 is an image taken by optical microscopy at 100× of a stent coated with the polyurethane (PU-NAP, example 5.2) of the invention sterilised and expanded.

To a stent previously weighted, a solution comprising the polyurethane polymer PU-NAP (Example 5.2) in dimethylsulfoxide was applied by immersion. The stent was thus coated with the solution. Hot air was applied and then the coated stent was cured at 60° C. for 24 hours. The coated stent comprised 229 μg of coating. The stent was crimped to a balloon catheter and it was sterilised with ethylene oxide. The stent was further unfolded at 18 atm, and it was visualized by optical microscopy at 100×. As can be deduced from FIG. 3, the coating was completely smooth and without delaminated (uncoated) points. No problems were detected when the balloon was unfolded.

Example 12

Polyamides Comprising the Compounds of Formula (I)

The compounds of formula (I) in which the radical X (X1 and/or X2) is an amino group may be used as reagents for the synthesis of polyamides.

Such a process includes the reaction of the compounds of formula (I) with a dicarboxylic acid or a salt thereof. Preferred dicarboxylic acids are selected from the group consisting of succinic acid and malic acid, or their salts with halogens, such as the chloride salt of the dicarboxylic acids.

The polyamide polymer obtainable by the process disclosed before, contains in its backbone the monomer units consisting in the compounds of formula (I) that contain a substance with anti-inflammatory, analgesic and/or anti-proliferative properties. The polyamide polymer, which comprises moreover a at least two amino terminal groups, may in turn be used in the synthesis of polyurethanes in the same way as the compounds of formula (I) with the diamine functionality and disclosed in Example 5.

The polyamide is synthesised following the Schotten-Baumann conditions, wherein the amine is reacted with the chloride salt of the dicarboxylic acid and an aqueous base is added to capture the acid generated in situ to improve the yield of the reaction. Thus to 3 moles of the compound of formula (Ie) solved in an appropriate solvent 2 mols of succinyl dichloride and 10 mols of triethylamine are added dropwise and simultaneously to obtain a polyamide with an average molecular weight of 1200 Da. The polyamide so obtained is useful for the synthesis of polyurethanes.

Example 13

Preparation of the Compound of Formula (If)

On the other hand, if the compound of formula (If) is desired to have as X1 and X2 the radical —OH, the demethylated naproxen is reacted with an appropriate compound of formula (III) leaving terminal —OH radicals after the deprotection step (removing of the corresponding P radical protective groups of compound of formula (III)).

Example 14

Preparation of a Compound of Formula (I) with Isocyanate Functionality

A compound of formula (Ie) is firstly reacted with hexamethyldisilazane (HMDS) to protect the amino groups and forming a trimethylsilazane (TMS) derivative. Secondly, the protected compound is filtered and the remaining solvent (dioxane) is evaporated at reduce pressure. Further, the protected compound is reacted with triphosgene in the presence of triethylamine and an anhydride aprotic solvent, such as diethyl ether or dioxane. The final product (compound of formula Ig) is isolated by filtration and distilled or recristalyzed. This synthetic route is derived from the one disclosed by Wiggins et. al, "Synthesis and characterization of L-lysine-based poly(ester urethane) networks", *Polymer Preprints,* 1992, vol. 33(2), pp. 516-517.

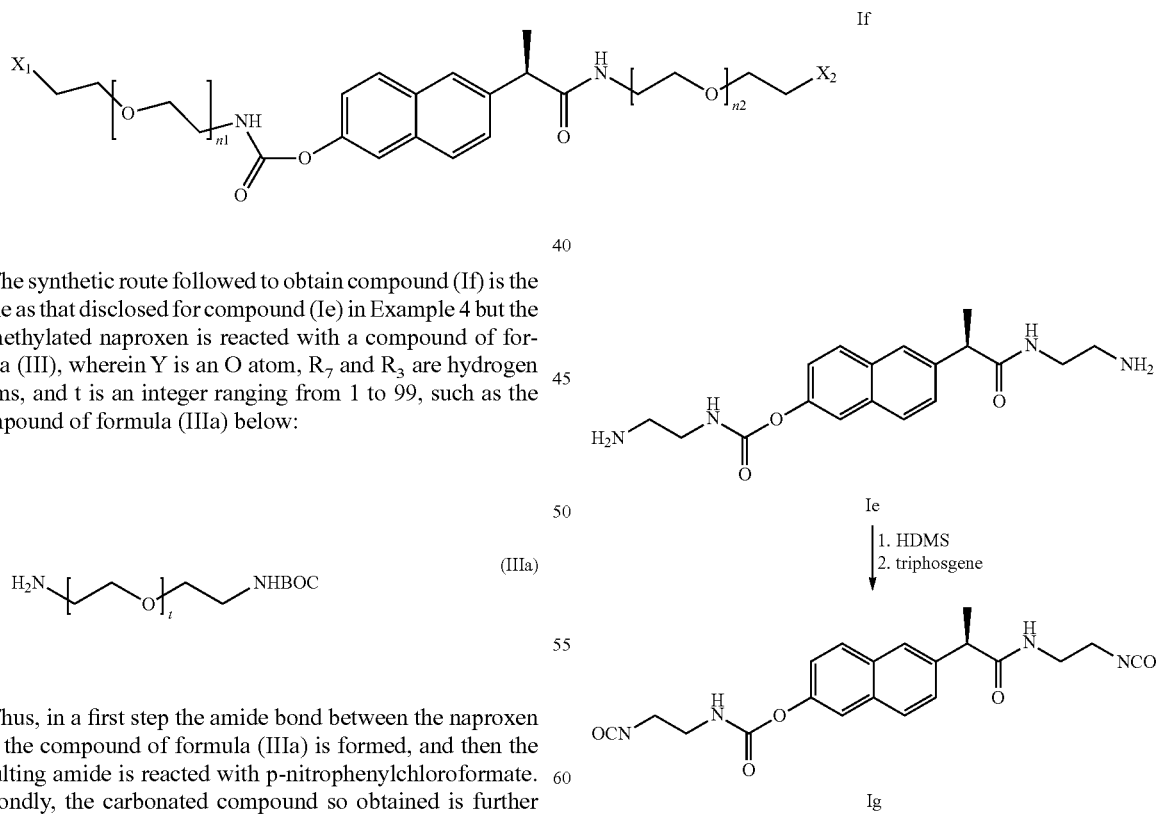

The synthetic route followed to obtain compound (If) is the same as that disclosed for compound (Ie) in Example 4 but the demethylated naproxen is reacted with a compound of formula (III), wherein Y is an O atom, $R_7$ and $R_3$ are hydrogen atoms, and t is an integer ranging from 1 to 99, such as the compound of formula (IIIa) below:

Thus, in a first step the amide bond between the naproxen and the compound of formula (IIIa) is formed, and then the resulting amide is reacted with p-nitrophenylchloroformate. Secondly, the carbonated compound so obtained is further reacted with the compound of formula (IIIa) and the terminal protective groups (BOC) are removed to obtain the compound (If) wherein X1 and X2 are amino radicals (—$NH_2$). As above exposed, if other X1 and X2 are desired, the amino groups may be transformed into another X radical, namely —NCO.

As indicated above, other suitable sequence of reactions may be done to obtain a compound with isocyanate functionality (—NCO terminal groups). Nonetheless, the herewith proposed route of synthesis is specially preferred since the protection of the amino groups with HMDS avoids undesirable polymerizations that can occur once the isocyanate compound is formed.

REFERENCES CITED IN THE APPLICATION

WO 2007/93662.
EP 1032605 B1.
Haag et al., "Polymer Therapeutics: Concepts and Applications", *Anqewandte Chemie*, 2006, vol. 45, pp. 1198-1215.
WO 2005/39489.
Gopin et. al., "Enzymatic Activation of Second-Generation Dendritic Prod rugs: Conjugation of Self-Inmolative Dendrimers with poly(ethylene glycol) via Click Chemistry", *Bioconjugate Chemistry*, 2006, vol. 17, pp. 1432-1440.
Jensen et. al., "Synthesis of Guanidium-Derived Receptor Libraries and Screening for Selective Peptide Receptors in Water", *Chemistry. A European Journal*, 2002, vol. 8, pp. 1300-1309.
Wiggins et. al., "Synthesis and characterization of L-lysine-based poly(ester urethane) networks", *Polymer Preprints*, 1992, vol. 33(2), pp. 516-517
WO 98/25938
Bratt et al., "Avenanthramides in Oats (*Avena sativa* L.) and Structure—Antioxidant Activity Relationships" *J. Agric. Food Chem*, 2003, vol. 51 (3), pp. 594-600

The invention claimed is:
1. A compound of formula (I) or a salt thereof,

    (I)(I)

wherein
-D is a radical derived from a drug or an active metabolite of a drug susceptible to form at least one of an amide bond, an urea bond, a carbamate bond, an ether bond, a thioamide bond, a disulfide bond, a siloxane bond, a carbonate bond, an amine bond, or an ester bond with S;
—S— is a biradical consisting of a branched or unbranched, saturated or unsaturated $C_2$-$C_{299}$ hydrocarbon chain, bonded for one extreme to radical X and for the other extreme susceptible to form at least one of an amide bond, an urea bond, a carbamate bond, an ether bond, a thioamide bond, a disulfide bond, a siloxane bond, a carbonate bond, an amine bond, or an ester bond with D, said hydrocarbon chain having at the extreme forming the bond with D an atom or group of atoms selected from the group consisting of an oxygen atom, a sulphur atom, a radical of formula $NR_2$ or a radical of formula CO, said hydrocarbon chain optionally having one or more non-terminal carbon atoms replaced by an oxygen atom, a sulphur atom, or group of formula $NR_2$, and wherein optionally at least one hydrogen atom of said hydrocarbon chain is substituted by at least one radical selected from the group consisting of an halogen or a $C_1$-$C_8$-alkyl radical;
—$R_2$ is a radical selected from the group consisting of hydrogen, and a linear or branched $C_1$-$C_8$-alkyl;
—X is a radical selected from the group consisting of —$NH_2$, NCO, and —OH; and
m is an integer from 2 to 4.
2. The compound of formula (I) according to claim 1, wherein the bond between D and S is an amide bond or a carbamate bond.
3. The compound of formula (I) according claim 1, wherein the $C_2$-$C_{299}$ hydrocarbon chain is a $C_2$-$C_8$ hydrocarbon chain.

4. The compound of formula (I) according to claim 3, wherein the $C_2$-$C_8$ hydrocarbon chain is a $C_2$ hydrocarbon chain.
5. The compound of formula (I) according to claim 1, wherein the $C_2$-$C_{299}$ hydrocarbon chain is a $C_2$-$C_{299}$ hydrocarbon chain with non-terminal carbon atoms replaced by oxygen atoms, which has the formula (II), wherein n is an integer ranging from 1 to 99, and the bonds crossed with sinusoidal lines represent the linkage point with the atoms or group of atoms that are finally forming any bond with the drug D or the radical X

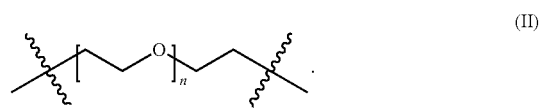    (II)

6. The compound of formula (I) according to claim 1, wherein X is an $NH_2$.
7. The compound of formula (I) according claim 1, which has the formula (Ia)

X1-S1-D-S2-X2    (Ia), wherein —X1 and —X2 are equal or different radicals having the same meaning as —X; —S1 and —S2 are equal or different radicals having the same meaning as —S; and -D, —X, and —S having the same meaning as in claim 1.
8. The compound according claim 1, wherein -D is a radical derived from a substance selected from the group consisting of homovanillic acid, 4-hydroxycinnamic acid, indomethacin, fendosal, diflunisal, p-coumaric acid, acemetacine, bentiromide, phenolphtalein, repaglinide, sarpogrelate, tiropropic acid, tiratricol, vanillic acid, 3-fluoro-4-hydroxyphenylacetic acid, iophenoic acid, allenolic acid, anacardic acid, cinnametic acid, cinmetacine, clometacine, ferulic acid, mycophenolic acid, salicylic acid, methyl salicylate, rhein, naproxen, and tranilast.
9. The compound according to claim 8, wherein -D is a radical derived from a substance selected from the group consisting of methyl salicylate, naproxen, and tranilast.
10. The compound according to claim 1, which is the compound of formula (Id)

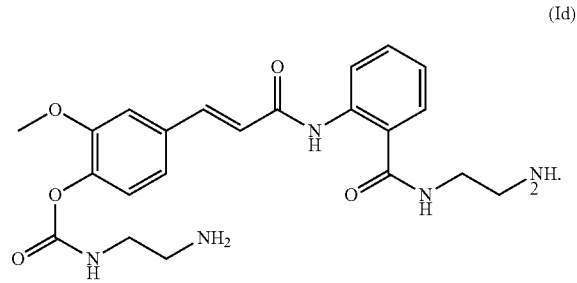    (Id)

11. The compound according to claim 1, which is the compound of formula (Ie)

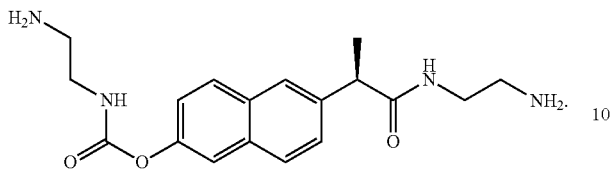
(Ie)

12. A process for preparing a compound of formula (I) as defined in claim 1, which comprises the steps of:
a) reacting a drug susceptible to form at least one of an amide bond, an urea bond, a carbamate bond, an ether bond, a thioamide bond, a disulfide bond, a siloxane bond, a carbonate bond, an amine bond, and an ester bond with a compound of formula (III),

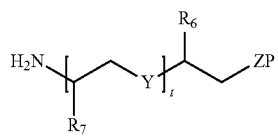
(III)

wherein:
—Y is an atom or group of atoms independently selected from the group consisting of $CH_2$, NH, O, and S;
-t is an integer ranging from 0 to 99;
—Z is an atom or group of atoms selected from the group consisting of NH and O; and
—P is a radical which is a protective group selected from the group consisting of t-butyloxycarbonyl, benzyl, allyl, t-butyl(chloro)diphenylsilane and $SiR_3R_4R_5$;
—$R_3$, —$R_4$, and —$R_5$ are radicals equal or different and selected from the group consisting of phenyl or lineal or branched $C_1$-$C_4$-alkyl;
—$R_6$ and $R_7$ are radicals equal or different and selected from the group consisting of hydrogen and methyl;
with the proviso that if Z is equal to O, P is selected from the group consisting of t-butyl(chloro)diphenylsilane and $SiR_3R_4R_5$, and if Z is equal to N, P is a radical selected from the group consisting of t-butyloxycarbonyl, benzyl and allyl; and
b) removing the protecting group by reaction of the compound obtained in step a) with an hydrogen halide in an appropriate solvent; to obtain a compound of formula (I) or, alternatively, c) reacting a drug susceptible to form at least one of an amide bond, an urea bond, a carbamate bond, an ether bond, a thioamide bond, a disulfide bond, a siloxane bond, a carbonate bond, an amine bond, or an ester bond, with a compound formula (IV), wherein T is an halogen atom;

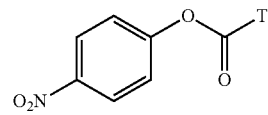
(IV)

d) reacting the compound obtained in step c) with a compound of formula (III); and
e) removing the P radical protecting group by reaction of the compound obtained in step d) with an hydrogen halide; to give a compound of formula (I)
or, alternatively,
f) reacting a drug susceptible to form at least one of an amide bond, an urea bond, a carbamate bond, an ether bond, a thioamide bond, a disulfide bond, a siloxane bond, a carbonate bond, an amine bond,
or an ester bond, with a compound of formula $(COW)_2$, wherein W is an halogen atom, in the presence of a compound of formula $C_1$-$C_4$alkyl-O-Q, wherein Q is an halogen atom;
g) reacting the compound obtained in step f) with sodium azide; and
h) hydrogenating the compound obtained in step g); to obtain a compound of formula (I);
and, if needed, repeating steps a) and b); or c), d) and e); or f), g) and h); or
a combination of a) and b) with c) d) and e); or a combination of a) and b) with f), g) and h);
or a combination of c) d) and e) with f), g) and h); to give a compound of formula (I) or a compound of formula (Ia) with m=2, 3 or 4;
wherein, optionally, the X radical of the compound of formula (I) obtained is transformed into another X radical of the compound of formula (I); and, optionally, the X1 or X2 radical of the compound of formula (Ia) obtained is transformed into another X1 or X2 radical of the compound of formula (Ia).

13. The process of claim 12, wherein in the compound of formula (I) obtained the radical D forms two bonds selected from the group consisting of an amide bond, an urea bond, a carbamate bond, an ether bond, a thioamide bond, a disulfide bond, a siloxane bond, a carbonate bond, an amine bond, and an ester bond.

\* \* \* \* \*